United States Patent
Dale et al.

(10) Patent No.: US 12,102,531 B2
(45) Date of Patent: Oct. 1, 2024

(54) TISSUE CUTTING SYSTEMS, DEVICES AND METHODS

(71) Applicant: Evalve, Inc., Santa Clara, CA (US)

(72) Inventors: Theodore Paul Dale, Corcoran, MN (US); Tracee Elizabeth Johnson Eidenschink, Wayzata, MN (US)

(73) Assignee: Evalve, Inc., Santa Clara, CA (US)

( * ) Notice: Subject to any disclaimer, the term of this patent is extended or adjusted under 35 U.S.C. 154(b) by 823 days.

(21) Appl. No.: 16/659,238

(22) Filed: Oct. 21, 2019

(65) Prior Publication Data

US 2020/0121460 A1 Apr. 23, 2020

Related U.S. Application Data

(60) Provisional application No. 62/748,947, filed on Oct. 22, 2018.

(51) Int. Cl.
*A61F 2/24* (2006.01)
*A61B 17/00* (2006.01)
(Continued)

(52) U.S. Cl.
CPC ............ *A61F 2/2445* (2013.01); *A61B 17/32* (2013.01); *A61B 18/1492* (2013.01); *A61F 2/2466* (2013.01); *A61B 2017/00243* (2013.01); *A61B 2017/00783* (2013.01); *A61B 2017/00867* (2013.01); *A61B 2018/00369* (2013.01);
(Continued)

(58) Field of Classification Search
CPC ...... A61F 2/2445; A61F 2/2466; A61F 2/246; A61F 2/2463; A61B 17/32; A61B 18/1492; A61B 2017/00243; A61B 2017/00783; A61B 2017/00867; A61B 2018/00369; A61B 2018/00601; A61B 2018/144; A61B 2018/1475; A61B 2017/003;
(Continued)

(56) References Cited

U.S. PATENT DOCUMENTS 1,996,261 A   4/1935  Storz
3,296,668 A   1/1967  Aiken
(Continued)

FOREIGN PATENT DOCUMENTS

CN   1469724    1/2004
CN   102770080  11/2012
(Continued)

OTHER PUBLICATIONS

Supplementary European Search Report issued in European Application No. 05753261.6 dated Jun. 9, 2011, 3 pages total.
(Continued)

*Primary Examiner* — Ronald Hupczey, Jr.
*Assistant Examiner* — Abigail Bock
(74) *Attorney, Agent, or Firm* — Workman Nydegger

(57) ABSTRACT

Methods, devices and systems for disabling and/or removing a mitral valve edge-to-edge repair device via minimally invasive, endovascular procedures. Additional procedures on a heart may sometimes become necessary after the installation of a mitral valve edge-to-edge repair device. To prepare for such additional procedures, the edge-to-edge repair device may be removed or disabled in minimally invasive ways (e.g., through an endovascular procedure), without requiring open access to the heart.

20 Claims, 21 Drawing Sheets

(51) Int. Cl.
    *A61B 17/32*     (2006.01)
    *A61B 18/00*     (2006.01)
    *A61B 18/14*     (2006.01)

(52) U.S. Cl.
    CPC .............. *A61B 2018/00601* (2013.01); *A61B 2018/144* (2013.01); *A61B 2018/1475* (2013.01)

(58) Field of Classification Search
    CPC .. A61B 2017/00358; A61B 2018/1407; A61B 2090/3966; A61B 17/1285
    See application file for complete search history.

(56) References Cited

U.S. PATENT DOCUMENTS

| | | | |
|---|---|---|---|
| 3,470,875 A | 10/1969 | Johnson et al. | |
| 3,671,979 A | 6/1972 | Moulopoulos | |
| 3,675,639 A | 7/1972 | Cimber | |
| 3,776,237 A | 12/1973 | Hill et al. | |
| 3,874,388 A | 4/1975 | King et al. | |
| 4,007,743 A | 2/1977 | Blake | |
| 4,056,854 A | 11/1977 | Boretos et al. | |
| 4,091,815 A | 5/1978 | Larsen | |
| 4,235,238 A | 11/1980 | Ogiu et al. | |
| 4,312,337 A | 1/1982 | Donahue | |
| 4,484,579 A | 11/1984 | Meno et al. | |
| 4,487,205 A | 12/1984 | Di Giovanni et al. | |
| 4,498,476 A | 2/1985 | Cerwin et al. | |
| 4,510,934 A | 4/1985 | Batra | |
| 4,531,522 A | 7/1985 | Bedi et al. | |
| 4,578,061 A | 3/1986 | Lemelson | |
| 4,641,366 A | 2/1987 | Yokoyama et al. | |
| 4,686,965 A | 8/1987 | Bonnet et al. | |
| 4,777,951 A | 10/1988 | Cribier et al. | |
| 4,809,695 A | 3/1989 | Gwathmey et al. | |
| 4,872,455 A | 10/1989 | Pinchuk et al. | |
| 4,878,495 A | 11/1989 | Grayzel | |
| 4,917,089 A | 4/1990 | Sideris | |
| 4,944,295 A | 7/1990 | Gwathmey et al. | |
| 4,969,890 A | 11/1990 | Sugita et al. | |
| 4,994,077 A | 2/1991 | Dobben | |
| 5,015,249 A | 5/1991 | Nakao et al. | |
| 5,042,707 A | 8/1991 | Taheri | |
| 5,047,041 A | 9/1991 | Samuels | |
| 5,049,153 A | 9/1991 | Nakao et al. | |
| 5,053,043 A | 10/1991 | Gottesman et al. | |
| 5,071,428 A | 10/1991 | Chin | |
| 5,069,679 A | 12/1991 | Taheri | |
| 5,078,722 A | 1/1992 | Stevens | |
| 5,078,723 A | 1/1992 | Dance et al. | |
| 5,171,259 A | 12/1992 | Inoue | |
| 5,190,554 A | 3/1993 | Coddington et al. | |
| 5,217,460 A | 6/1993 | Knoepfler | |
| 5,226,911 A | 7/1993 | Chee et al. | |
| 5,254,130 A | 10/1993 | Poncet et al. | |
| 5,282,845 A | 2/1994 | Bush et al. | |
| 5,318,525 A | 6/1994 | West et al. | |
| 5,320,632 A | 6/1994 | Heidmueller | |
| 5,332,402 A | 7/1994 | Teitelbaum | |
| 5,336,227 A | 8/1994 | Nakao et al. | |
| 5,342,393 A | 8/1994 | Stack | |
| 5,350,399 A | 9/1994 | Erlebacher et al. | |
| 5,368,601 A | 11/1994 | Sauer et al. | |
| 5,373,854 A | 12/1994 | Kolozsi | |
| 5,387,219 A | 2/1995 | Rappe | |
| 5,391,182 A | 2/1995 | Chin | |
| 5,395,030 A | 3/1995 | Kuramoto et al. | |
| 5,403,326 A | 4/1995 | Harrison et al. | |
| 5,411,552 A | 5/1995 | Andersen et al. | |
| 5,417,684 A | 5/1995 | Jackson et al. | |
| 5,417,699 A | 5/1995 | Klein et al. | |
| 5,417,700 A | 5/1995 | Egan | |
| 5,423,830 A | 6/1995 | Schneebaum et al. | |
| 5,423,857 A | 6/1995 | Rosenman et al. | |
| 5,423,882 A | 6/1995 | Jackman et al. | |
| 5,431,666 A | 7/1995 | Sauer et al. | |
| 5,450,860 A | 9/1995 | O'Connor | |
| 5,456,400 A | 10/1995 | Shichman et al. | |
| 5,456,684 A | 10/1995 | Schmidt et al. | |
| 5,472,423 A | 12/1995 | Gronauer | |
| 5,478,353 A | 12/1995 | Yoon | |
| 5,496,332 A | 3/1996 | Sierra et al. | |
| 5,507,755 A | 4/1996 | Gresl et al. | |
| 5,507,757 A | 4/1996 | Sauer et al. | |
| 5,522,873 A | 6/1996 | Jackman et al. | |
| 5,527,322 A | 6/1996 | Klein et al. | |
| 5,536,251 A | 7/1996 | Evard et al. | |
| 5,542,949 A | 8/1996 | Yoon | |
| 5,554,185 A | 9/1996 | Block et al. | |
| 5,562,678 A * | 10/1996 | Booker | A61B 17/221 |
| | | | 606/127 |
| 5,569,274 A | 10/1996 | Rapacki et al. | |
| 5,571,085 A | 11/1996 | Accisano, III | |
| 5,571,137 A | 11/1996 | Marlow et al. | |
| 5,571,215 A | 11/1996 | Sterman et al. | |
| 5,582,611 A | 12/1996 | Tsuruta et al. | |
| 5,584,803 A | 12/1996 | Stevens et al. | |
| 5,609,598 A | 3/1997 | Laufer et al. | |
| 5,617,854 A * | 4/1997 | Munsif | A61M 25/0041 |
| | | | 606/50 |
| 5,618,306 A | 4/1997 | Roth et al. | |
| 5,620,461 A | 4/1997 | Muijs Van De Moer et al. | |
| 5,626,588 A | 5/1997 | Sauer et al. | |
| 5,636,634 A | 6/1997 | Kordis et al. | |
| 5,649,937 A | 7/1997 | Bito et al. | |
| 5,662,681 A | 9/1997 | Nash et al. | |
| 5,669,917 A | 9/1997 | Sauer et al. | |
| 5,669,919 A | 9/1997 | Sanders et al. | |
| 5,690,671 A | 11/1997 | McGurk et al. | |
| 5,695,504 A | 12/1997 | Gifford, III et al. | |
| 5,695,505 A | 12/1997 | Yoon | |
| 5,706,824 A | 1/1998 | Whittier | |
| 5,709,707 A | 1/1998 | Lock et al. | |
| 5,716,367 A | 2/1998 | Koike et al. | |
| 5,718,725 A | 2/1998 | Sterman et al. | |
| 5,722,421 A | 3/1998 | Francese et al. | |
| 5,725,542 A | 3/1998 | Yoon | |
| 5,725,556 A | 3/1998 | Moser et al. | |
| 5,741,271 A | 4/1998 | Nakao et al. | |
| 5,741,280 A | 4/1998 | Fleenor | |
| 5,746,747 A | 5/1998 | McKeating | |
| 5,749,828 A | 5/1998 | Solomon et al. | |
| 5,769,812 A | 6/1998 | Stevens et al. | |
| 5,769,863 A | 6/1998 | Garrison | |
| 5,782,845 A | 7/1998 | Shewchuk | |
| 5,797,927 A | 8/1998 | Yoon | |
| 5,797,960 A | 8/1998 | Stevens et al. | |
| 5,810,849 A | 9/1998 | Kontos | |
| 5,810,876 A | 9/1998 | Kelleher | |
| 5,820,591 A | 10/1998 | Thompson et al. | |
| 5,820,630 A | 10/1998 | Lind | |
| 5,823,956 A | 10/1998 | Roth et al. | |
| 5,829,447 A | 11/1998 | Stevens et al. | |
| 5,836,955 A | 11/1998 | Buelna et al. | |
| 5,840,081 A | 11/1998 | Andersen et al. | |
| 5,843,103 A | 12/1998 | Wulfman | |
| 5,853,422 A | 12/1998 | Huebsch et al. | |
| 5,855,590 A | 1/1999 | Malecki et al. | |
| 5,855,614 A | 1/1999 | Stevens et al. | |
| 5,860,990 A | 1/1999 | Nobles et al. | |
| 5,861,003 A | 1/1999 | Latson et al. | |
| 5,891,160 A | 4/1999 | Williamson, IV et al. | |
| 5,895,404 A | 4/1999 | Ruiz | |
| 5,895,417 A | 4/1999 | Pomeranz et al. | |
| 5,906,620 A | 5/1999 | Nakao et al. | |
| 5,908,420 A | 6/1999 | Parins | |
| 5,947,363 A | 9/1999 | Bolduc et al. | |
| 5,954,732 A | 9/1999 | Hart et al. | |
| 5,957,949 A | 9/1999 | Leonhard et al. | |
| 5,957,973 A | 9/1999 | Quiachon et al. | |
| 5,972,020 A | 10/1999 | Carpentier et al. | |
| 5,972,030 A | 10/1999 | Garrison et al. | |
| 5,980,455 A | 11/1999 | Daniel et al. | |

(56) References Cited

U.S. PATENT DOCUMENTS

| | | |
|---|---|---|
| 5,989,284 A | 11/1999 | Laufer |
| 5,997,547 A | 12/1999 | Nakao et al. |
| 6,007,546 A | 12/1999 | Snow et al. |
| 6,022,360 A | 2/2000 | Reimels et al. |
| 6,033,419 A | 3/2000 | Hamblin et al. |
| 6,053,933 A | 4/2000 | Balazs et al. |
| 6,056,769 A | 5/2000 | Epstein et al. |
| 6,063,106 A | 5/2000 | Gibson |
| 6,066,146 A | 5/2000 | Carroll et al. |
| 6,090,118 A | 7/2000 | McGuckin, Jr. |
| 6,099,553 A | 8/2000 | Hart et al. |
| 6,117,144 A | 9/2000 | Nobles et al. |
| 6,117,159 A | 9/2000 | Huebsch et al. |
| 6,123,665 A | 9/2000 | Kawano |
| 6,136,010 A | 10/2000 | Modesitt et al. |
| 6,139,508 A | 10/2000 | Simpson |
| 6,143,024 A | 11/2000 | Campbell et al. |
| 6,162,233 A | 12/2000 | Williamson, IV et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,174,322 B1 | 1/2001 | Schneidt |
| 6,180,059 B1 | 1/2001 | Divino, Jr. et al. |
| 6,197,043 B1 | 3/2001 | Davidson |
| 6,203,553 B1 | 3/2001 | Robertson et al. |
| 6,206,893 B1 | 3/2001 | Klein et al. |
| 6,206,907 B1 | 3/2001 | Marino et al. |
| 6,245,079 B1 | 6/2001 | Nobles et al. |
| 6,264,617 B1 | 7/2001 | Bales et al. |
| 6,267,781 B1 | 7/2001 | Tu |
| 6,269,819 B1 | 8/2001 | Oz et al. |
| 6,283,127 B1 | 9/2001 | Sterman et al. |
| 6,299,637 B1 | 10/2001 | Shaolian et al. |
| 6,312,447 B1 | 11/2001 | Grimes |
| 6,319,250 B1 | 11/2001 | Falwell et al. |
| 6,332,893 B1 | 12/2001 | Mortier et al. |
| 6,334,860 B1 | 1/2002 | Dorn |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,640 B1 | 7/2002 | Taylor |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,494,881 B1 | 12/2002 | Bales et al. |
| 6,508,828 B1 | 1/2003 | Akerfeldt et al. |
| 6,517,550 B1 | 2/2003 | Konya et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,921 B2 | 9/2003 | Blatter et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,932,810 B2 | 8/2005 | Ryan |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen III et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,056,294 B2 | 6/2006 | Khairkhahan et al. |
| 7,112,207 B2 | 9/2006 | Allen et al. |
| 7,226,467 B2 | 6/2007 | Lucatero et al. |
| 7,258,694 B1 | 8/2007 | Choi et al. |
| 7,288,097 B2 | 10/2007 | Seguin |
| 7,291,168 B2 | 11/2007 | Macoviak et al. |
| 7,338,467 B2 | 3/2008 | Lutter |
| 7,381,210 B2 | 6/2008 | Zarbatany et al. |
| 7,435,257 B2 | 10/2008 | Lashinski et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,955,340 B2 | 6/2011 | Michlitsch |
| 8,216,234 B2 | 7/2012 | Long |
| 8,257,356 B2 | 9/2012 | Bleich et al. |
| 8,398,708 B2 | 3/2013 | Meiri et al. |
| 8,435,237 B2 | 5/2013 | Bahney |
| 8,496,655 B2 | 7/2013 | Epp et al. |
| 8,500,768 B2 | 8/2013 | Cohen |
| 8,523,881 B2 | 9/2013 | Cabiri et al. |
| 8,623,077 B2 | 1/2014 | Cohn |
| 8,690,858 B2 | 4/2014 | Machold et al. |
| 8,821,518 B2 | 9/2014 | Saliman et al. |
| 8,926,588 B2 | 1/2015 | Berthiaume et al. |
| 9,126,032 B2 | 9/2015 | Khairkhahan et al. |
| 9,211,119 B2 | 12/2015 | Hendricksen |
| 9,370,341 B2 | 6/2016 | Ceniccola et al. |
| 9,498,331 B2 | 11/2016 | Chang et al. |
| 9,572,666 B2 | 2/2017 | Basude et al. |
| 9,770,256 B2 | 9/2017 | Cohen et al. |
| 9,949,833 B2 | 4/2018 | McCleary et al. |
| 10,238,493 B1 | 3/2019 | Metchik et al. |
| 10,667,804 B2 | 6/2020 | Basude et al. |
| 11,013,554 B2* | 5/2021 | Coates ............. A61B 18/1492 |
| 11,406,250 B2* | 8/2022 | Saadat ............. A61B 1/00085 |
| 2001/0002445 A1 | 5/2001 | Vesely |
| 2001/0005787 A1 | 6/2001 | Oz et al. |
| 2001/0010005 A1 | 7/2001 | Kammerer et al. |
| 2001/0037084 A1 | 11/2001 | Nardeo |
| 2001/0044568 A1 | 11/2001 | Langberg et al. |
| 2001/0044635 A1 | 11/2001 | Niizeki et al. |
| 2002/0013547 A1 | 1/2002 | Paskar |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |

(56) References Cited

U.S. PATENT DOCUMENTS

| | | |
|---|---|---|
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0103532 A1 | 8/2002 | Langberg et al. |
| 2002/0147456 A1 | 10/2002 | Diduch et al. |
| 2002/0156526 A1 | 10/2002 | Hilavka et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0074012 A1 | 4/2003 | Nguyen et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030319 A1* | 2/2004 | Korkor ............ A61M 25/0074 604/506 |
| 2004/0030382 A1 | 2/2004 | St. Goar et al. |
| 2004/0034380 A1 | 2/2004 | Woolfson et al. |
| 2004/0039442 A1 | 2/2004 | St. Goar et al. |
| 2004/0044350 A1* | 3/2004 | Martin ............... A61B 17/0469 606/139 |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059345 A1 | 3/2004 | Nakao et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0116951 A1 | 6/2004 | Rosengart |
| 2004/0122448 A1 | 6/2004 | Levine |
| 2004/0127849 A1 | 7/2004 | Kantor |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0153144 A1 | 8/2004 | Seguin |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225233 A1 | 11/2004 | Frankowski et al. |
| 2004/0225300 A1 | 11/2004 | Goldfarb et al. |
| 2004/0225305 A1 | 11/2004 | Ewers et al. |
| 2004/0225353 A1 | 11/2004 | McGuckin et al. |
| 2004/0236354 A1 | 11/2004 | Seguin |
| 2004/0242960 A1 | 12/2004 | Orban |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0065453 A1 | 3/2005 | Shabaz et al. |
| 2005/0085903 A1 | 4/2005 | Lau |
| 2005/0119735 A1 | 6/2005 | Spence et al. |
| 2005/0131438 A1 | 6/2005 | Cohn |
| 2005/0143809 A1 | 6/2005 | Salahieh et al. |
| 2005/0149014 A1 | 7/2005 | Hauck et al. |
| 2005/0159763 A1 | 7/2005 | Mollenauer |
| 2005/0159810 A1 | 7/2005 | Filsoufi |
| 2005/0192633 A1 | 9/2005 | Montpetit |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | DeMarchi et al. |
| 2005/0267493 A1 | 12/2005 | Schreck et al. |
| 2005/0273160 A1 | 12/2005 | Lashinski et al. |
| 2005/0277876 A1 | 12/2005 | Hayden |
| 2006/0004247 A1 | 1/2006 | Kute et al. |
| 2006/0009759 A1 | 1/2006 | Chrisitian et al. |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020334 A1 | 1/2006 | Lashinski et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0135993 A1 | 6/2006 | Seguin |
| 2006/0184198 A1 | 8/2006 | Bales |
| 2006/0184203 A1 | 8/2006 | Martin et al. |

(56) References Cited

U.S. PATENT DOCUMENTS

| | | |
|---|---|---|
| 2006/0195012 A1 | 8/2006 | Mortier et al. |
| 2006/0229708 A1* | 10/2006 | Powell ............... A61B 17/0401 623/1.24 |
| 2006/0252984 A1 | 11/2006 | Randert et al. |
| 2006/0276890 A1* | 12/2006 | Solem .................. A61F 2/2451 623/2.36 |
| 2007/0016225 A1 | 1/2007 | Nakao |
| 2007/0038293 A1 | 2/2007 | St. Goer et al. |
| 2007/0060997 A1 | 3/2007 | de Boer |
| 2007/0073185 A1 | 3/2007 | Nakao |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0173757 A1 | 7/2007 | Levine et al. |
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2007/0287884 A1 | 12/2007 | Schena |
| 2008/0009858 A1 | 1/2008 | Rizvi |
| 2008/0039935 A1 | 2/2008 | Buch et al. |
| 2008/0045936 A1 | 2/2008 | Vaska et al. |
| 2008/0051703 A1 | 2/2008 | Thorton et al. |
| 2008/0051807 A1 | 2/2008 | St. Goar et al. |
| 2008/0097467 A1 | 4/2008 | Gruber et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0243249 A1 | 10/2008 | Kohm et al. |
| 2008/0294175 A1 | 11/2008 | Bardsley et al. |
| 2008/0312496 A1 | 12/2008 | Zwolinski |
| 2009/0012538 A1 | 1/2009 | Saliman et al. |
| 2009/0036768 A1 | 2/2009 | Seehusen et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0192510 A1 | 7/2009 | Bahney |
| 2009/0198322 A1 | 8/2009 | Deem et al. |
| 2009/0204005 A1 | 8/2009 | Keast et al. |
| 2009/0209955 A1 | 8/2009 | Forster et al. |
| 2009/0209991 A1 | 8/2009 | Hinchliffe et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0044410 A1 | 2/2010 | Argentine et al. |
| 2010/0121437 A1 | 5/2010 | Subramanian et al. |
| 2010/0152612 A1 | 6/2010 | Headley et al. |
| 2010/0217261 A1 | 8/2010 | Watson |
| 2010/0262231 A1 | 10/2010 | Tuval et al. |
| 2010/0268226 A1 | 10/2010 | Epp et al. |
| 2010/0298929 A1 | 11/2010 | Thornton et al. |
| 2011/0009864 A1 | 1/2011 | Bucciaglia et al. |
| 2011/0184405 A1 | 7/2011 | Mueller |
| 2011/0224710 A1 | 9/2011 | Bleich |
| 2011/0238052 A1 | 9/2011 | Robinson |
| 2012/0022527 A1 | 1/2012 | Woodruff |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0157765 A1 | 6/2012 | Mitelberg |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0310330 A1 | 12/2012 | Buchbinder et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0109910 A1 | 5/2013 | Alexander et al. |
| 2013/0172828 A1 | 7/2013 | Kappel et al. |
| 2013/0317515 A1 | 11/2013 | Kuroda et al. |
| 2014/0039511 A1 | 2/2014 | Morris et al. |
| 2014/0135799 A1 | 5/2014 | Henderson |
| 2014/0228871 A1 | 8/2014 | Cohen et al. |
| 2014/0276913 A1 | 9/2014 | Tah et al. |
| 2014/0309670 A1 | 10/2014 | Bakos et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0364866 A1 | 12/2014 | Dryden et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0051698 A1 | 2/2015 | Ruyra Baliarda et al. |
| 2015/0094800 A1 | 4/2015 | Chawla |
| 2015/0112430 A1 | 4/2015 | Creaven et al. |
| 2015/0211946 A1 | 7/2015 | Pons et al. |
| 2015/0230947 A1 | 8/2015 | Krieger et al. |
| 2015/0257877 A1 | 9/2015 | Hernandez |
| 2015/0306806 A1 | 10/2015 | Dando et al. |
| 2015/0313581 A1 | 11/2015 | Wolfe et al. |
| 2016/0015410 A1 | 1/2016 | Asirvatham et al. |
| 2016/0074165 A1 | 3/2016 | Spence et al. |
| 2016/0174979 A1 | 6/2016 | Wei |
| 2016/0317174 A1 | 11/2016 | Dake |
| 2017/0042678 A1 | 2/2017 | Ganesan et al. |
| 2017/0100183 A1 | 4/2017 | Iaizzo et al. |
| 2017/0202559 A1 | 7/2017 | Taha |
| 2017/0232238 A1 | 8/2017 | Biller et al. |
| 2018/0008268 A1* | 1/2018 | Khairkhahan ......... A61B 17/10 |
| 2018/0028215 A1 | 2/2018 | Cohen |
| 2018/0092661 A1 | 4/2018 | Prabhu |
| 2018/0133010 A1 | 5/2018 | Kizuka |
| 2018/0161159 A1 | 6/2018 | Lee |
| 2018/0360457 A1 | 12/2018 | Ellis et al. |
| 2019/0029790 A1 | 1/2019 | Bak-Boychuk et al. |
| 2019/0183571 A1 | 6/2019 | De Marchena |
| 2019/0298517 A1 | 10/2019 | Sanchez et al. |
| 2019/0307458 A1* | 10/2019 | Mathis ............... A61B 1/00148 |
| 2021/0113232 A1 | 4/2021 | Ortiz et al. |
| 2021/0145574 A1 | 5/2021 | Childs et al. |

FOREIGN PATENT DOCUMENTS

| | | |
|---|---|---|
| CN | 103841899 | 6/2014 |
| CN | 104244841 A | 12/2014 |
| DE | 3504292 | 7/1986 |
| DE | 9100873 U1 | 4/1991 |
| DE | 10116168 | 11/2001 |
| EP | 0179562 | 7/1989 |
| EP | 0558031 | 2/1993 |
| EP | 0684012 | 11/1995 |
| EP | 0727239 | 8/1996 |
| EP | 0782836 | 7/1997 |
| EP | 1674040 | 6/2006 |
| EP | 1980288 | 10/2008 |
| EP | 2005912 | 12/2008 |
| EP | 2537487 | 12/2012 |
| EP | 2641570 | 9/2013 |
| EP | 2702965 | 3/2014 |
| EP | 2740419 A1 | 6/2014 |
| EP | 3009103 | 4/2016 |
| FR | 2705556 | 12/1994 |
| FR | 2768324 | 3/1999 |
| FR | 2903292 A1 | 1/2008 |
| GB | 1598111 | 9/1981 |
| GB | 2151142 | 7/1985 |
| JP | 2001-517529 A | 10/2001 |
| JP | 2006528911 | 12/2006 |
| JP | 2013516244 | 5/2013 |
| JP | 2014523274 | 9/2014 |
| JP | 2018-030008 A | 3/2018 |
| WO | WO 1981000668 | 3/1981 |
| WO | WO 1991001689 | 2/1991 |
| WO | WO 1994018881 | 9/1994 |
| WO | WO 1994018893 | 9/1994 |
| WO | WO 1995008292 | 3/1995 |
| WO | WO 1995011620 | 5/1995 |
| WO | WO 1995015715 | 6/1995 |

(56) References Cited

FOREIGN PATENT DOCUMENTS

| | | |
|---|---|---|
| WO | WO 1996020655 | 7/1996 |
| WO | WO 1996022735 | 8/1996 |
| WO | WO 1996030072 | 10/1996 |
| WO | WO 1997018746 | 5/1997 |
| WO | WO 1997025927 | 7/1997 |
| WO | WO 1997026034 | 7/1997 |
| WO | WO 1997038748 | 10/1997 |
| WO | WO 1997039688 | 10/1997 |
| WO | WO 1997048436 | 12/1997 |
| WO | WO 1998007375 | 2/1998 |
| WO | WO 1998024372 | 6/1998 |
| WO | WO 1998030153 | 7/1998 |
| WO | WO 1998032382 | 7/1998 |
| WO | WO 1998035638 | 8/1998 |
| WO | WO 1999000059 | 1/1999 |
| WO | WO 1999001377 | 1/1999 |
| WO | WO 1999007295 | 2/1999 |
| WO | WO 1999013777 | 3/1999 |
| WO | WO 1999044524 | 9/1999 |
| WO | WO 2000003651 | 1/2000 |
| WO | WO 2000003759 | 1/2000 |
| WO | WO 2000012168 | 3/2000 |
| WO | WO 2000044313 | 8/2000 |
| WO | WO 2000060995 | 10/2000 |
| WO | WO 2001000114 | 1/2001 |
| WO | WO 2001026557 | 4/2001 |
| WO | WO 2001028432 | 4/2001 |
| WO | WO 2001028455 | 4/2001 |
| WO | WO 2001047438 | 7/2001 |
| WO | WO 2001049213 | 7/2001 |
| WO | WO 2001050985 | 7/2001 |
| WO | WO 2001054618 | 8/2001 |
| WO | WO 2001066001 | 9/2001 |
| WO | WO 2001070320 | 9/2001 |
| WO | WO 2001089440 | 11/2001 |
| WO | WO 2002000099 | 1/2002 |
| WO | WO 2002001999 | 1/2002 |
| WO | WO 2002003892 | 1/2002 |
| WO | WO 2002034167 | 5/2002 |
| WO | WO 2002060352 | 8/2002 |
| WO | WO 2002062263 | 8/2002 |
| WO | WO 2003001893 | 1/2003 |
| WO | WO 2003003930 | 1/2003 |
| WO | WO 2003020179 | 3/2003 |
| WO | WO 2003028558 | 4/2003 |
| WO | WO 2003037171 | 5/2003 |
| WO | WO 2003047467 | 6/2003 |
| WO | WO 2003049619 | 6/2003 |
| WO | WO 2003073913 | 9/2003 |
| WO | WO 2003105667 | 12/2003 |
| WO | WO 2004006810 | 1/2004 |
| WO | WO 2004012583 | 2/2004 |
| WO | WO 2004012789 | 2/2004 |
| WO | WO 2004014282 | 2/2004 |
| WO | WO 2004019811 | 3/2004 |
| WO | WO 2004030570 | 4/2004 |
| WO | WO 2004037317 | 5/2004 |
| WO | WO 2004045370 | 6/2004 |
| WO | WO 2004045378 | 6/2004 |
| WO | WO 2004045463 | 6/2004 |
| WO | WO 2004062725 | 7/2004 |
| WO | WO 2004082523 | 9/2004 |
| WO | WO 2004082538 | 9/2004 |
| WO | WO 2004103162 | 12/2004 |
| WO | WO 2004112585 | 12/2004 |
| WO | WO 2005018507 | 3/2005 |
| WO | WO 2005032421 | 4/2005 |
| WO | WO 2005062931 | 7/2005 |
| WO | WO 2005112792 | 12/2005 |
| WO | WO 2006037073 | 4/2006 |
| WO | WO 2006105008 | 10/2006 |
| WO | WO 2006105009 | 10/2006 |
| WO | WO 2006113906 | 10/2006 |
| WO | WO 2006115876 | 11/2006 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | WO 2013049734 | 4/2013 |
| WO | WO 2013103934 | 7/2013 |
| WO | WO 2014064694 | 5/2014 |
| WO | WO 2014121280 | 8/2014 |
| WO | WO 2016022797 | 2/2016 |
| WO | WO 2016144708 | 9/2016 |
| WO | WO 2016150806 | 9/2016 |
| WO | WO 2017223073 | 12/2017 |
| WO | WO 2018009718 | 1/2018 |
| WO | WO 2018106482 | 6/2018 |
| WO | 2018/236766 A1 | 12/2018 |
| WO | 2019/040943 A1 | 2/2019 |
| WO | 2019/195336 A1 | 10/2019 |

OTHER PUBLICATIONS

Nishimura, et al. 2014 AHA/ACC guideline for the management of patients with valvular heart disease: executive summary: a report of the American College of Cardiology/American Heart Association Task Force on Practice Guidelines. J Am Coll Cardiol. Jun. 10, 2014; 63(22):2438-88.

Abe et al, "De Vega's Annuloplasty for Acquired Tricuspid Disease: Early and Late Results in 110 Patients", Ann. Thorac. Surg., pp. 670-676, vol. 48 (Jan. 1989).

Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).

Alfieri et al., "An Effective Technique to Correct Anterior Mitral Leaflet Prolapse," J. Card Surg., 14:468-470 (1999).

Alfieri et al., "Novel Suture Device for Beating Heart Mitral Leaflet Approximation," Annals of Thoracic Surgery, 74:1488-1493 (2002).

Alfieri et al., "The edge to edge technique," The European Association for Cardio-Thoracic Surgery 14th Annual Meeting, Oct. 7-11, 2000, Book of Proceedings.

Ali Khan et al, Blade Atrial Septostomy: Experience with the First 50 Procedures, Cathet. Cardiovasc. Diagn., Aug. 1991, pp. 257-262, vol. 23.

Alvarez et al, Repairing the Degenerative Mitral Valve: Ten to Fifteen-year Follow-up, Journal of Thoracic Cardiovascular Surgery, Aug. 1996, pp. 238-247, vol. 112, No. 2.

Bailey, "Mitral Regurgitation" in Surgery of the Heart, Chapter 20, pp. 686-737 (1955).

Borghetti et al., "Preliminary observations on haemodynamics during physiological stress conditions following 'double-orifice' mitral valve repair," European Journal of Cardio-thoracic Surgery, 20:262-269 (2001).

Castedo, "Edge-to-Edge Tricuspid Repair for Redeveloped Valve Incompetence after DeVega's Annuloplasty," Ann Thora Surg., 75:605-606 (2003).

Chinese Office Action issued in Chinese Application No. 200980158707.2 dated Sep. 9, 2013.

Communication dated Apr. 16, 2018 from the European Patent Office in counterpart European application No. 04752603.3.

Communication dated Apr. 28, 2017 issued by the European Patent Office in counterpart application No. 16196023.2.

Communication dated Jan. 26, 2017, from the European Patent Office in counterpart European application No. 16196023.2.

Dang N C et al., "Surgical Revision After Percutaneous Mitral Valve Repair with a Clip: Initial Multicenter Experience",The Annals of Thracic Surgery,Elsevier, United States, vol. 80, No. 6, pp. 2338-2342, (Dec. 1, 2005), XP027732951, ISSN:0003-4975 [retrieved on Dec. 1, 2005].

Dottori et al., "Echocardiographic imaging of the Alfieri type mitral valve repair," Ital. Heart J., 2(4):319-320 (2001).

Downing et al., "Beating heart mitral valve surgery: Preliminary model and methodology," Journal of Thoracic and Cardiovascular Surgery, 123(6):1141-1146 (2002).

Extended European Search Report, dated Oct. 17, 2014, issued in European Patent Application No. 06751584.1.

(56) References Cited

OTHER PUBLICATIONS

Falk et al., "Computer-Enhanced Mitral Valve Surgery: Toward a Total Endoscopic Procedure," Seminars in Thoracic and Cardiovascular Surgery, 11(3):244-249 (1999).
Feldman et al, Randomized Comparison of Percutaneous Repair and Surgery for Mitral Regurgitation: 5-Year Results of Everest II. J Am Coll Cardiol. Dec. 29, 2015; 66(25):2844-2854.
Fucci et al, Improved Results with Mitral Valve Repair Using New Surgical Techniques, Eur. J. Cardiothorac. Surg., Nov. 1995, pp. 621-627, vol. 9.
Garcia-Rinaldi et al., "Left Ventricular Volume Reduction and Reconstruction is Ischemic Cardiomyopathy," Journal of Cardiac Surgery, 14:199-210 (1999).
Izzat et al., "Early Experience with Partial Left Ventriculectomy in the Asia-Pacific Region," Annuals of Thoracic Surgery, 67:1703-1707 (1999).
Kallner et al., "Transaortic Approach for the Alfieri Stitch," Ann Thorac Surg, 71:378-380 (2001).
Kavarana et al., "Transaortic Repair of Mitral Regurgitation," The Heart Surgery Forum, #2000-2389, 3(1):24-28 (2000).
Khan et al., "Blade Atrial Septostomy; Experience with the First 50 Procedures", Catheterization and Cardiovascular Diagnosis, 23:257-262 (1991).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Maisano et al., "Valve Repair for Traumatic Tricuspid Regurgitation," Eur. J. Cardio-Thorac Surg, 10:867-873 (1996).
Maisano et al., "The Edge-to-edge Technique: A Simplified Method to Correct Mitral Insufficiency", Eur. J. Cardiothorac. Surg., pp. 240-246, vol. 13 ( Jan. 14, 1998).
Maisano et al., "The Double Orifice Repair for Barlow Disease: a Simple Solution for a Complex Repair," Supplement I Circulation, 100(18):1-94 (Nov. 1999).
Maisano et al., "The Double Orifice Technique as a Standardized Approach to Treat Mitral Regurgitation due to Severe Myxomatous Disease: Surgical Technique," European Journal of Cardio-thoracic Surgery, 17:201-205 (2000).
Maisano et al., "The Future of Transcatheter Mitral Valve Interventions: Competitive or Complementary Role of Repair vs. Replacement?", Eur Heart J.36(26):1651-1659 ( Jul. 7, 2015 ).
Mantovani et al., "Edge-to-edge Repair of Congenital Familiar Tricuspid Regurgitation: Case Report," J. Heart Valve Dis., 9:641-643 (2000).
McCarthy et al, "Tricuspid Valve Repair With the Cosgrove-Edwards Annuloplasty System", Ann. Thorac. Surg., 64:267-8 ( Jan. 16, 1997).
McCarthy et al., "Partial Left Ventriculectomy and Mitral Valve Repair for End-Stage Congestive Heart Failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Nishimura et al, 2014 AHA/ACC guideline for the management of patients with valvular heart disease: executive summary: a report of the American College of Cardiology/American Heart Association Task Force on Practice Guidelines. J Am Coll Cardiol. Jun. 10, 2014; 63(22):2438-2488.

Park et al., Clinical Use of Blade Atrial Septostomy, Circulation, pp. 600-608, vol. 58, No. 4 (1978 ).
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Rose et al., "Late MitraClip Failure: Removal Technique for Leaflet-Sparing Mitral Valve Repair", Journal of Cardiac Surgery, (Jul. 4, 2012), XP055047339, DOI: 10.1111/j. 1540-8191.2012.01483.x [retrieved on Dec. 11, 2012].
Takizawa H et al: "Development of a microfine active bending catheter equipped with MIF tactile sensors", Micro Electro Mechanical Systems, 1999. MEMS '99. Twelfth IEEE Interna Tional Conference On Orlando, FL, USA Jan. 17-21, 1999, Piscataway, NJ, USA, IEEE, US, Jan. 17, 1999 (Jan. 17, 1999), pp. 412-417, XP010321677, ISBN: 978-0-7803-5194-3 figures 1-3.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Timek et al., "Edge-to-edge mitral repair: gradients and three-dimensional annular dynamics in vivo during inotropic stimulation," Eur J. of Cardiothoracic Surg., 19:431-437 (2001).
Totaro, "Mitral valve repair for isolated prolapse of the anterior leaflet: an 11-year follow-up," European Journal of Cardio-thoracic Surgery, 15:119-126 (1999).
Uchida et al., Percutaneous Cardiomyotomy and Valvulotomy with Angioscopic Guidance, Am. Heart J., pp. 1221-1224, vol. 121 (Apr. 1991).
Umana et al., 'Bow-Tie' Mitral Valve Repair: An Adjuvant Technique for Ischemic Mitral Regurgitation, Ann. Thorac. Surg., pp. 1640-1646, vol. 66 (May 12, 1998).
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 14/216,787, Apr. 8, 2016, Office Action.
U.S. Appl. No. 14/216,787, Nov. 7, 2016, Notice of Allowance.
U.S. Appl. No. 14/216,813, Mar. 9, 2017, Office Action.
U.S. Appl. No. 14/216,813, Dec. 15, 2017, Office Action.
U.S. Appl. No. 14/216,813, Apr. 6, 2018, Office Action.
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 15/423,060, Apr. 25, 2019, Office Action.
U.S. Appl. No. 15/423,060, Aug. 19, 2019, Office Action.
U.S. Appl. No. 15/423,060, Oct. 28, 2019, Office Action.
U.S. Appl. No. 15/423,060, Jan. 27, 2020, Notice of Allowance.
U.S. Appl. No. 15/642,245, Aug. 9, 2019, Office Action.
U.S. Appl. No. 15/642,245, Nov. 6, 2019, Notice of Allowance.
U.S. Appl. No. 15/642,245, Jan. 29, 2019, Notice of Allowance.
U.S. Appl. No. 15/642,245, Mar. 27, 2020, Notice of Allowance.
U.S. Appl. No. 15/724,545, Dec. 27, 2019, Office Action.
U.S. Appl. No. 15/724,545, May 1, 2020, Office Action.
Alfieri et al., "The double orifice technique in mitral valve repair: a simple solution for complex problems," Journal of Thoracic and Cardiovascular Surgery, 122:674-681 (2001).
Bhudia et al., "Edge-to-Edge (Alfieri) Mitral Repair: Results in Diverse Clinical Settings," Ann Thorac Surg, 77:1598-1606 (2004).
Maisano et al., The future of transcatheter mitral valve interventions: competitive or complementary role of repair vs. replacement? Eur Heart J. Jul. 7, 2015; 36(26):1651-1659.
Tager et al., Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
U.S. Provisional Application filed Jul. 6, 2016, by Khairkhahan., U.S. Appl. No. 62/359,121.

(56) References Cited

OTHER PUBLICATIONS

U.S. Provisional Application filed Nov. 7, 2016, by Khairkhahan., U.S. Appl. No. 62/418,571.
U.S. Provisional Application filed Oct. 22, 2018, by Dale et al., U.S. Appl. No. 62/748,947.

* cited by examiner

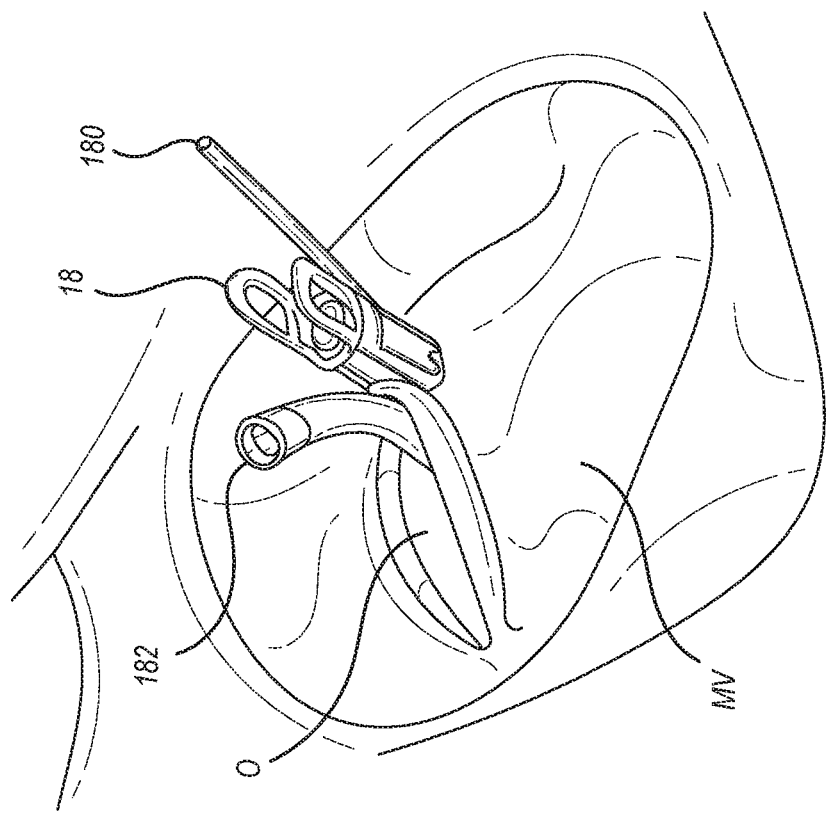
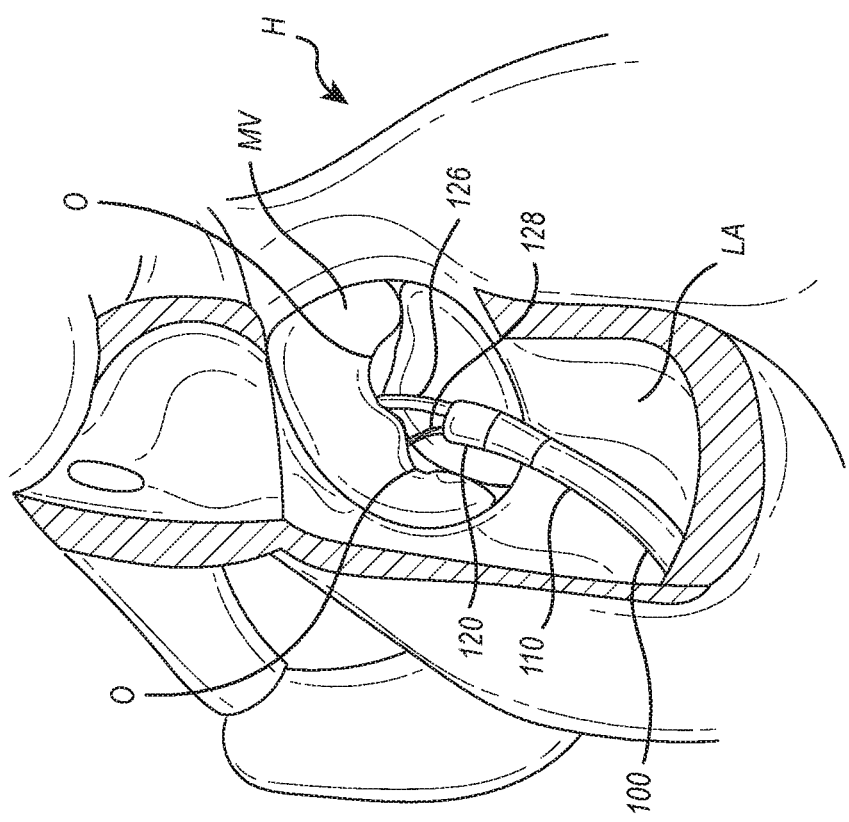

TISSUE CUTTING SYSTEMS, DEVICES AND METHODS

CROSS-REFERENCE TO RELATED APPLICATIONS

This application claims the benefit of priority based on U.S. Provisional Patent Application Ser. No. 62/748,947, filed Oct. 22, 2018 and entitled "Leaflet Cutting Devices and Methods."

BACKGROUND

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to cutting of leaflet tissue in preparation of subsequent implanting of a medical implant through minimally invasive procedures.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from many different mechanical defects in the mitral valve or the left ventricular wall. The valve leaflets, the valve chordae which connect the leaflets to the papillary muscles, the papillary muscles themselves or the left ventricular wall may be damaged or otherwise dysfunctional. Commonly, the valve annulus may be damaged, dilated, or weakened, limiting the ability of the mitral valve to close adequately against the high pressures of the left ventricle.

One treatment for mitral valve regurgitation relies on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular or Abbott Structural Heart, Santa Clara, Calif., USA.

However, sometimes after a fixation device is installed, undesirable mitral valve regurgitation can still exist, or can arise again. Further, other problems with the heart may arise that can make it desirable for the fixation device to be disabled or removed, usually in order that other procedures may be performed on the heart.

Current techniques for removing or disabling mitral valve fixation devices usually rely on open heart surgery where the patient's chest is opened, typically via a sternotomy, and the patient placed on cardiopulmonary bypass, which can pose a high risk of complications and extended patient recovery times.

For these reasons, it would be desirable to provide alternative and additional methods, devices, and systems for removing or disabling previously installed fixation devices. Such methods, devices, and systems should preferably not require open chest access and be capable of being performed either endovascularly, i.e., using devices which are advanced to the heart from a point in the patient's vasculature remote from the heart, or by another minimally invasive approach. The methods, devices, and systems may be useful for repair of tissues in the body other than heart valves. At least some of these objectives will be met by the inventions described hereinbelow.

BRIEF SUMMARY

The present disclosure describes methods, devices and systems that may be employed to detach a previously sutured "bowtie" or implanted device that clips together the anterior and posterior leaflets of a valve from one or all of the leaflets. The technology described and claimed herein could also be adapted to selectively target and cut tissue in other areas of the human anatomy via similar endovascular procedures.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which:

FIGS. 18A and 18B illustrate partial cut-away views of a human heart from the atrial side and from the ventricular side, respectively, showing distal portions of a cutting member and a capture member passing through orifices in the mitral valve from the left atrium into the left ventricle.

DETAILED DESCRIPTION

As mentioned earlier, sometimes, after installation of an edge-to-edge repair device, such as a suture "bow-tie" or fixation device, in the heart, it needs to be removed or at least detached from one or both of anterior and posterior leaflets. Ordinarily, this has been done during a high-risk invasive procedure such as open-heart surgery. The presently described system 100, and associated devices and methods, however, allow a physician or clinician to address heart problems in a minimally invasive procedure.

Figure 1:
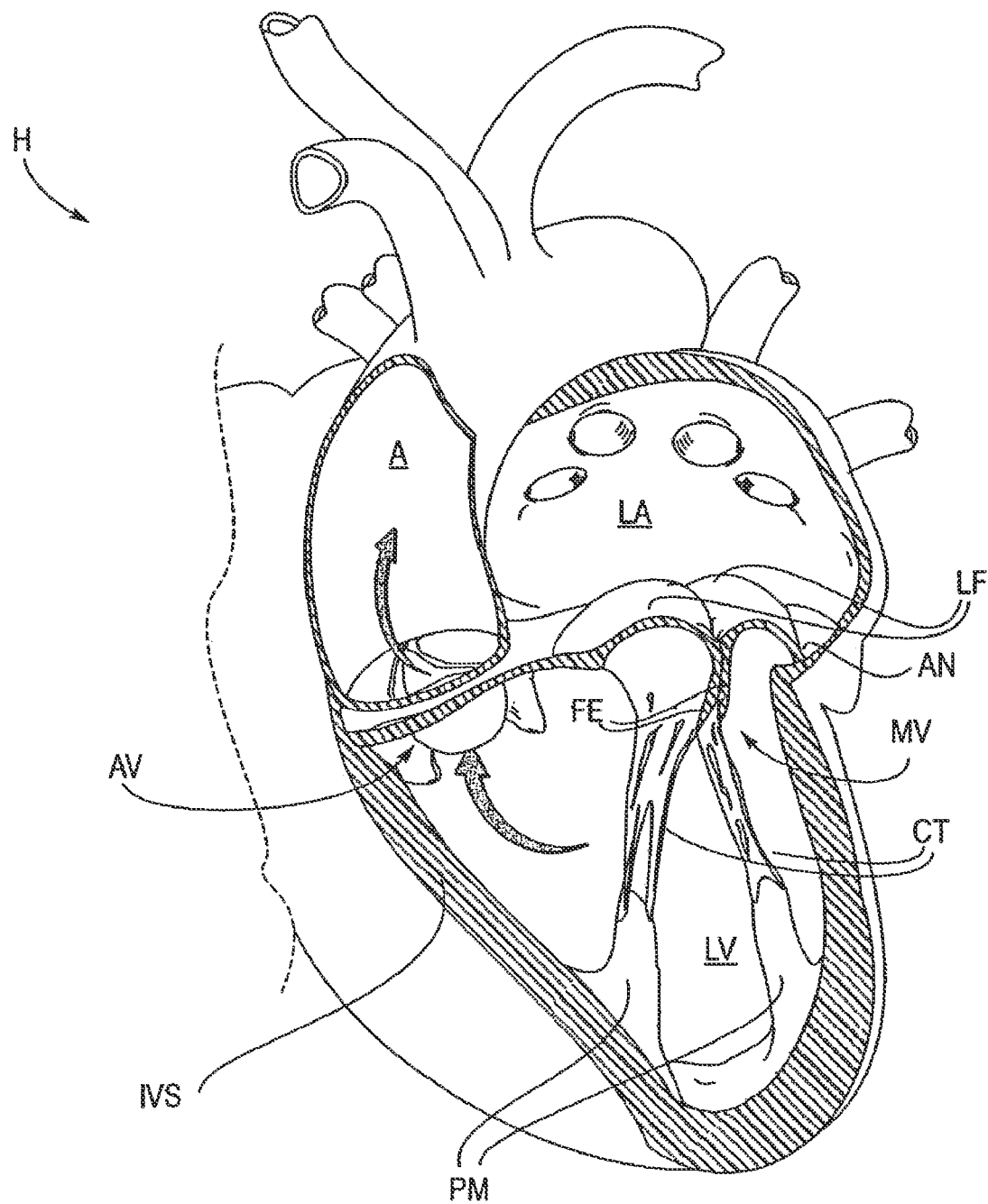
FIG. 1 illustrates the left ventricle and left atrium of the heart during systole.

For ease of explanation, FIG. 1 illustrates the left ventricle (LV) of a normal heart H in systole. The left ventricle (LV) is contracting and blood flows outwardly through the tricuspid (aortic) valve (AV) in the direction of the arrows. Back flow of blood or "regurgitation" through the mitral valve (MV) is prevented since the mitral valve is configured as a "check valve" which prevents back flow when pressure in the left ventricle is higher than that in the left atrium (LA). The mitral valve (MV) comprises a pair of leaflets having free edges (FE) which meet evenly to close, as illustrated in FIG. 1. The opposite ends of the leaflets (LF) are attached to the surrounding heart structure along an annular region referred to as the annulus (AN). The free edges (FE) of the leaflets (LF) are secured to the lower portions of the left ventricle LV through chordae tendinae (CT) (referred to hereinafter as the chordae) which include a plurality of branching tendons secured over the lower surfaces of each of the valve leaflets (LF). The chordae (CT) in turn, are attached to the papillary muscles (PM) which extend upwardly from the lower portions of the left ventricle and intraventricular septum IVS.

Figure 2A:
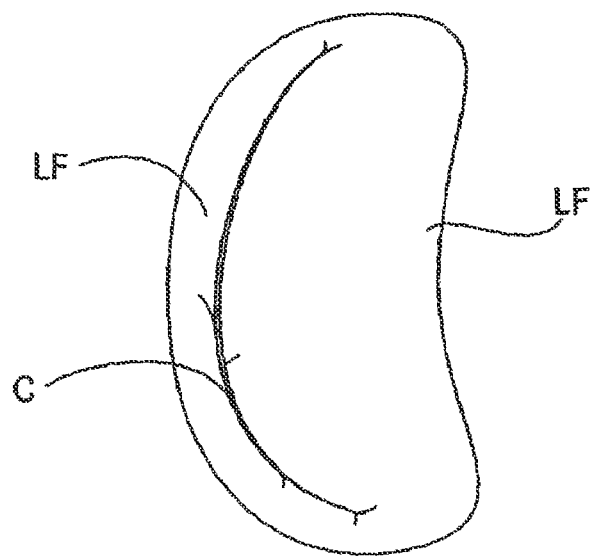
FIG. 2A illustrates free edges of leaflets of the mitral valve in normal coaptation.
Figure 2B:
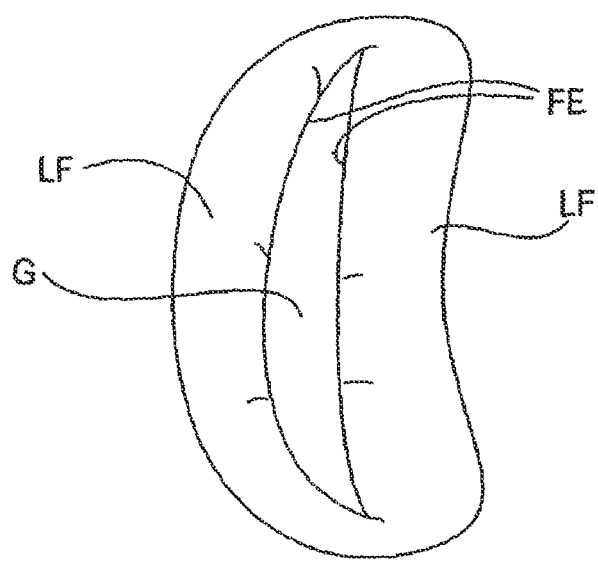
FIG. 2B illustrates the free edges in regurgitative coaptation.

Several structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation (C). An example of a defect causing regurgitation is shown in FIG. 2B. Here an enlargement of the heart causes the mitral annulus to become enlarged, making it impossible for the free edges (FE) to meet during systole. This results in a gap (G) which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

Various fixation devices are used for grasping, approximating and fixating tissues, such as valve leaflets, to treat cardiac valve regurgitation, particularly mitral valve regurgitation. Certain fixation devices are described in in U.S. Pat. No. 7,563,267, which is incorporated herein by this reference. The fixation devices may rely upon the use of an interventional tool that is positioned near a desired treatment site and used to grasp the target tissue. In endovascular applications, the interventional tool is typically an interventional catheter. In surgical applications, the interventional tool is typically an interventional instrument. Fixation of the grasped tissue is accomplished by maintaining grasping with a portion of the interventional tool which is left behind as an implant. The fixation devices are well adapted for the repair of valves, especially cardiac valves such as the mitral valve.

Figure 3A:
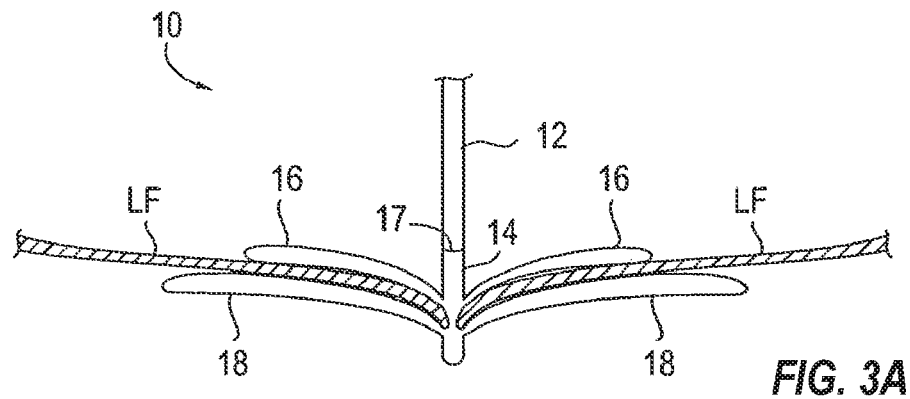
FIGS. 3A-3C illustrate grasping of the leaflets with a fixation device, inversion of the distal elements of the fixation device, and removal of the fixation device, respectively.

Referring to FIG. 3A, an interventional tool 10, having a delivery device, such as a shaft 12, and a fixation device 14, is schematically illustrated having approached the mitral valve MV from the atrial side and grasped the leaflets LF. The mitral valve may be accessed either surgically or by using endovascular techniques, and either by a retrograde approach through the ventricle or by an antegrade approach through the atrium, as described above. For illustration purposes, an antegrade approach is described.

The fixation device 14 (sometimes also referred to herein as a "suture 'bow-tie'" or an "edge-to-edge repair device") is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown to capture or retain the leaflets therebetween. The proximal elements 16 are preferably comprised of cobalt chromium, nitinol or stainless steel, and the distal elements 18 are preferably comprised of cobalt chromium or stainless steel, however any suitable materials may be used. The fixation device 14 is coupleable to the shaft 12 by a coupling mechanism 17. The coupling mechanism 17 allows the fixation device 14 to detach and be left behind as an implant to hold the leaflets together in the coapted position.

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 may be released and optionally inverted to a configuration suitable for withdrawal of the device 14 from the valve without tangling or interfering with or damaging the chordae, leaflets or other tissue. According to another embodiment, any of the endovascular methods described herein for disabling or removal of the fixation device may also be used.

Figure 3B:
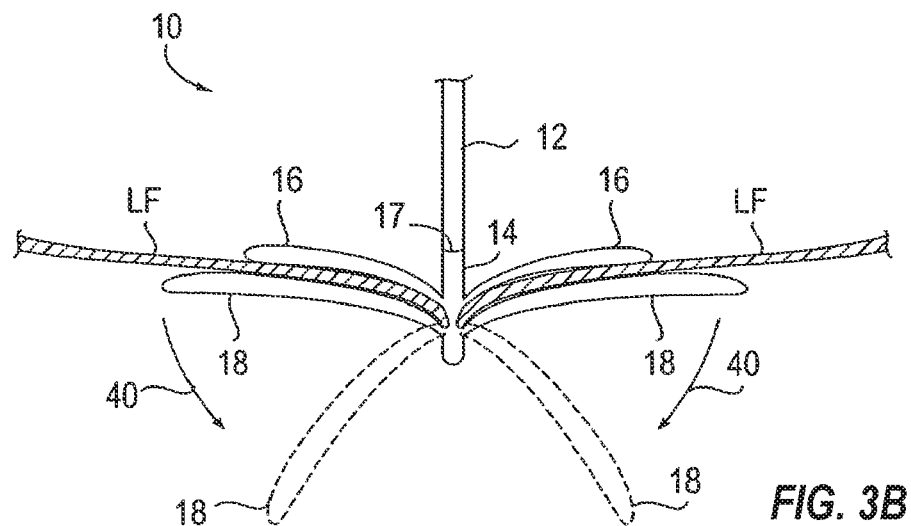
Figure 3C:
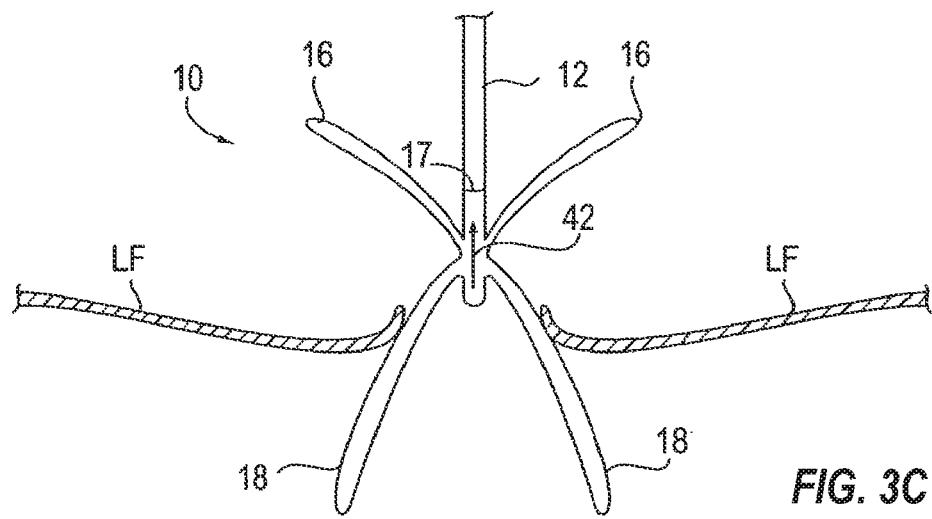

FIG. 3B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 3A. Alternatively, the fixation device 14 may be withdrawn (indicated by arrow 42) from the leaflets as shown in FIG. 3C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 4:
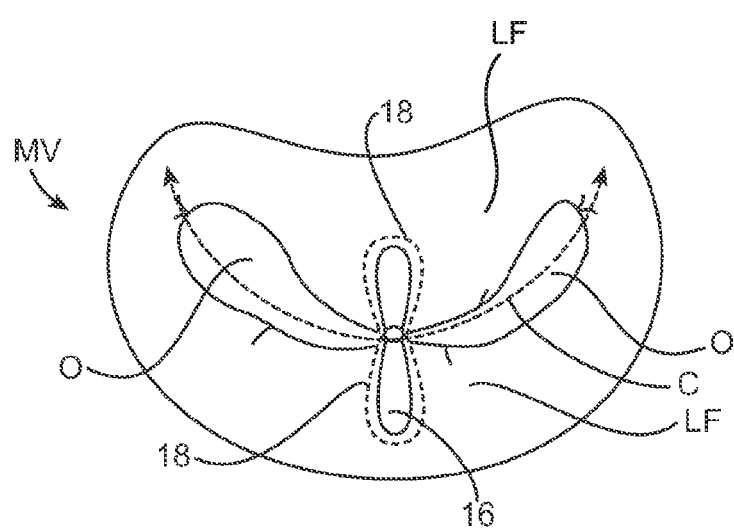
FIG. 4 illustrates the position of the fixation device in a desired orientation relative to the leaflets.

FIG. 4 illustrates the position of the fixation device 14 in a desired orientation in relation to the leaflets LF. This is a short-axis view of the mitral valve MV from the atrial side, therefore, the proximal elements 16 are shown in solid line and the distal elements 18 are shown in dashed line. The proximal and distal elements 16, 18 are positioned to be substantially perpendicular to the line of coaptation C. The device 14 may be moved roughly along the line of coaptation to the location of regurgitation. The leaflets LF are held in place so that during diastole, as shown in FIG. 4, the leaflets LF remain in position between the elements 16, 18 surrounded by openings or orifices O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together to be in contact with one another or may be held slightly apart but will preferably be maintained in the vertical orientation in which the upstream surfaces face each other at the point of coaptation. This simulates the double orifice geometry of a standard surgical "bow-tie" repair where the edges of the leaflets are brought into apposition and sutured together to form the double orifice. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place.

Once the leaflets are coapted in the desired arrangement, the fixation device 14 is then detached from the shaft 12 and left behind as an implant to hold the leaflets together in the coapted position.

Additional examples of interventional tools and systems and fixation devices are described in in U.S. Pat. No. 7,563,267, which is incorporated herein by this reference.

Sometimes, after construction of the suture "bow-tie" or installation of one or more fixation devices in the heart, it needs to be removed or at least detached from one or both of anterior and posterior leaflets. Ordinarily, this has been done during an invasive procedure such as open-heart surgery. Invasive procedures such as these often have high risk of complications. Further, sometimes mitral valve fixation devices, or the suture "bow-tie," are installed on patients for whom open-heart or more invasive procedures are otherwise unnecessary or undesirable. For these patients, and even for patients in whom open-heart surgery is used, it would be beneficial to have devices and systems specifically designed for removing or at least detaching the suture "bow-tie" or fixation devices from one or both of anterior and posterior leaflets within an endovascular procedure, rather than a procedure requiring open heart access.

Minimally invasive systems, methods, and devices for removing or at least detaching the suture "bow-tie" or fixation devices from one or both of anterior and posterior leaflets are disclosed herein. These minimally invasive systems, methods, and devices allow a practitioner to remove or at least detaching the suture "bow-tie" or fixation devices from one or both of anterior and posterior leaflets and, optionally, then proceed to do perform other medical procedures in the heart, without necessarily requiring open heart access or other more invasive procedures. Such systems, methods, and devices are configured to be effective even if the suture "bow-tie" or fixation device has been installed for weeks, months, or years, such that tissue surrounding the device may have grown over, into, or around the suture "bow-tie" or fixation device.

An embodiment of the present invention discloses systems that can include guidewires, catheters and other components that can perform various specific functions, and also multifunctional catheters that can perform any combination of functions. Such functions may include holding or retaining an installed fixation device or the suture "bow-tie"; cutting a leaflet or leaflets; removing the suture "bow-tie" or a fixation device; and repairing the leaflet(s). Related methods for performing such functions are also disclosed.

The mitral valve may be accessed using the systems, methods, and devices disclosed and/or claimed herein either surgically or by using endovascular techniques, and either by a retrograde approach through the ventricle or by an antegrade approach through the atrium, as described above. For illustration purposes, an antegrade approach is described.

The devices and associated methods and systems described herein may be used in combination with imaging modalities such as x-ray, fluoroscopy, echocardiography, charge coupled device cameras, complementary metal oxide semiconductor cameras, magnetic resonance imaging, and other imaging modalities. The availability of such imaging modalities during such procedures may help practitioners visualize, for example, where the fixation devices are, how they are connected to the heart, and where to direct the various catheters and/or other devices.

Figure 5:
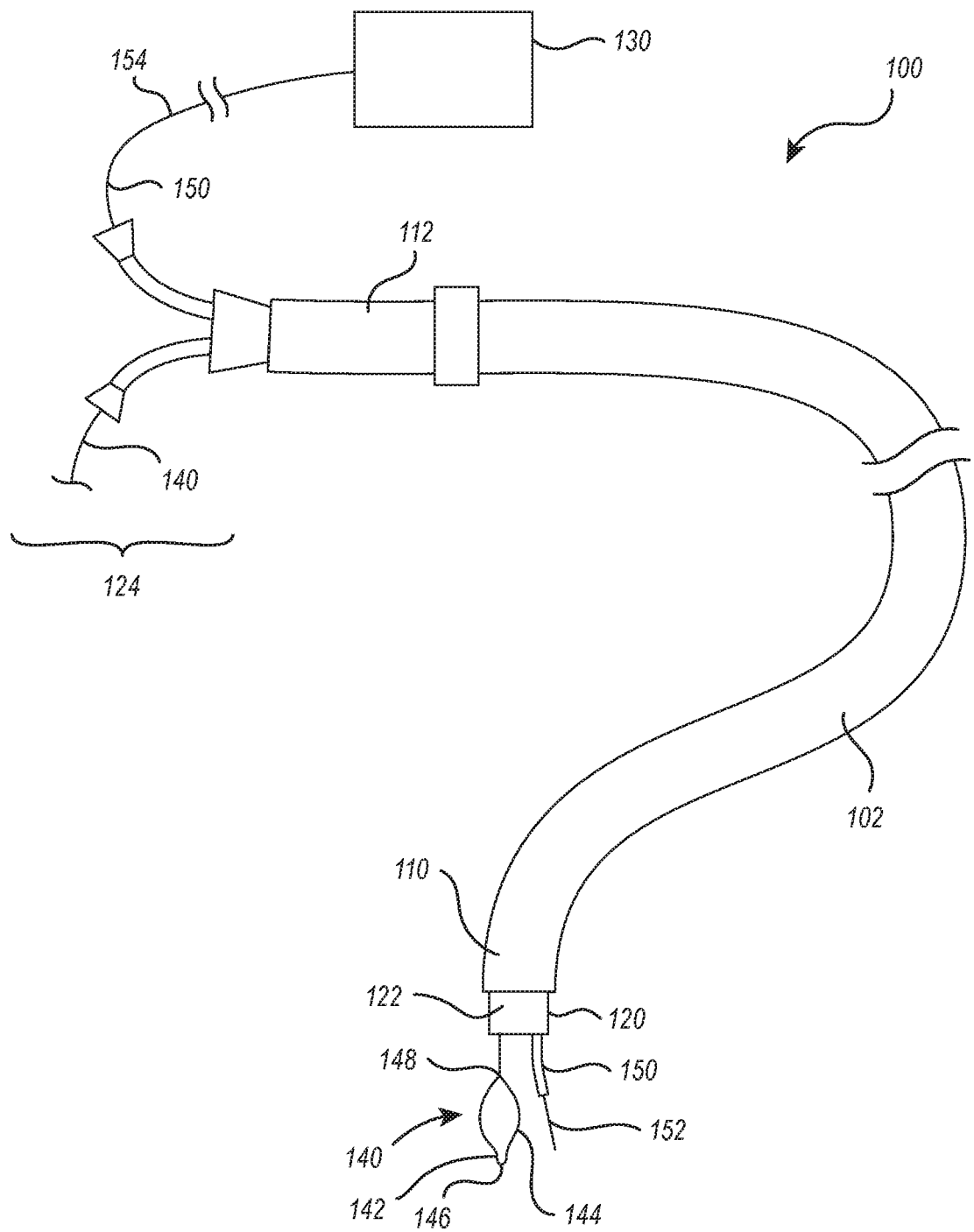
FIG. 5 illustrates a system for detaching an edge-to-edge repair device from one or more leaflets.

FIG. 5 illustrates a system 100 that may be used to at least detach an edge-to-edge repair device, such as a suture "bow-tie" or a fixation device, from at least one of the anterior and posterior leaflets LF. The system 100 can achieve this without open access to the heart, via a minimally invasive intravascular procedure, and through a single transseptal puncture. It will be understood, however, that the system 100 can also be used to detach a suture "bow-tie" or a fixation device from both or all leaflets to which the fixation device is attached. Furthermore, the system 100 can be used with the suture "bow-tie" or fixation devices identified herein or various other devices that are used to repair the leaflets, such as during an edge-to-edge repair. The suture "bow-tie" or fixation devices can be considered as edge-to-edge repair devices.

As illustrated, the system 100 can take the form of an elongate member 102, such as a multicomponent catheter, which is adapted to be advanced through a patient's vasculature. Elongate member or catheter 102 can include a guiding catheter 110 through which a delivery catheter 120 can be advanced to a previously implanted edge-to-edge repair device (not shown). The guiding catheter 110 can be, in one configuration, a steerable catheter or introducer, such as a Steerable Introducer sold under the trademark AGILIS.

The guiding catheter 110 can be steered through the tortuous anatomy to the heart and, using a transseptal approach, advanced through the septum between the right and left atria toward the mitral valve (MV). Once in place, the guiding catheter 110, whether alone or in combination with the delivery catheter 120, can position a distal end 122 of the delivery catheter 120 relative to the mitral valve (MV) for performing edge-to-edge repair device detachment as described herein. The steerability of guiding catheter 110 can be achieved through any number of known structures and methods, including but not limited to those disclosed in U.S. Pat. No. 7,653,267. In some embodiments, delivery catheter 120 can also move axially relative to the guide catheter. In other embodiments, a distal end portion of delivery catheter 120 can also be steerable independent of, and in a different plane from, guiding catheter 110.

The delivery catheter 120 accommodates a capturing member 140 and a cutting member 150 that extends from a proximal end 124 to the distal end 122. The capturing member 140, such as a snare, is used to capture and aid with positioning a cutting region of the cutting member 150 relative to the tissue to be cut to detach the edge-to-edge repair device from the leaflets LF. As discussed in additional detail below, withdrawing the capturing member 140 into the delivery catheter 120, while at the same time advancing the cutting member 150, provides the desired looping and positioning of the cutting member 150 so that the cutting region of the cutting member 150 can be used to cut the leaflets.

To aid with such capturing, as illustrated in FIG. 5, the capturing member 140 can include a looped portion 144 at a distal end 142. This looped portion 144 can include a narrowed portion 146 that facilitates preferential collapsing of the capturing member 140 when the capturing member 140 draws the cutting member 150 into the distal end 122 of the delivery catheter 120. For instance, two halves of the looped portion 144 can collapse together with the narrowed portion 146 acting as a hinge or pivot that aids with the left and right sides moving together as the distal end 122 of the delivery catheter 120 contacts a proximal end 148 of the looped portion 144. It will be understood that other structures can be formed in the looped portion 144 to aid with the preferential collapsing. For instance, a wire forming the snare can be ground or narrowed to preferentially bend.

While FIG. 5 illustrates the capturing member 140 having the looped portion 144, other types of capturing mechanisms may include, but are not limited to, for example, sheaths, conduits, expandable baskets, vacuums, magnets, vices, and clamps. For instance, the capturing member 140 and the cutting member 150 can include magnets or be formed of materials that magnetically attract so that the distal end 152 of the cutting member 150 might be attracted to the distal end 142 of the capturing member 140 or vice versa.

The capturing member 140 can be a wire, tubular member, or other elongate structure and can be made of metal, plastic, shape-memory alloys or polymers, or any suitable material, e.g., such as those described herein (e.g., cobalt-chromium alloys, stainless steel, nickel-titanium, Elgiloy®, etc.

A distal end portion of capturing member 140 can include a pre-formed, resilient, shape-memory loop configuration and/or orientation, such as looped portion 144. The loop can collapse and straighten when held within the constraints of the delivery catheter 120. Once advanced distally beyond the distal end of the delivery catheter 120, the loop can self-expand and return to its pre-formed, shape-memory configuration and orientation.

Capturing member 140 can also include one or more radiopaque markers positioned adjacent and/or around the looped portion 144. As discussed in additional detail below, such radiopaque markers assist in locating and visualizing the location, position and orientation of such capturing member 140 and cutting member 150, as well as their respective locations, positions and orientations relative to one another.

The cutting member 150 can electrically communicate with an electrosurgical device 130 (such as an electrosurgical generator), which can selectively provide radio-frequency energy to the cutting member 150. The cutting member 150, therefore, can function as a probe electrode that can cut, coagulate, desiccate, and fulgurate tissue, such as the leaflets LF. More particularly, the cutting member 150 can be used to cut at least a portion of at least one of the anterior and posterior leaflets LF or other tissue to which the edge-to-edge repair device is coupled.

The cutting member 150 can include a conductive core 158 with an electrically insulating coating 160 formed over at least a portion of the core 158. In some configurations the cutting member 150 is a guide wire that includes a proximal end 154 that can be electrically connected or coupled to an electrosurgical device 130, which can be used to selectively apply electrical energy to cutting member 150. The electrical cooperation can occur through an uncoated or exposed portion 159 at the proximal end 154 of core 158, which can be connected to electrosurgical device 130. Additional details regarding the cutting member 140 will be provided in connection with FIGS. 6-9 below.

Portions of capturing member 140 and cutting member 150 can also include good torque characteristics. In other words, when rotational forces are applied at their respective proximal ends to cause rotational movement at the proximal ends, such rotational movement is translated relatively closely to the respective distal ends. In this manner, the relative positioning and orientation of the distal end of capturing member 140 (including any pre-formed bends or curves and/or loop 144) and the distal end of cutting member (including any pre-formed bends or curves) can be closely correlated to the rotational position of the corresponding proximal ends thereof.

System 100 can also include a handle or fixture, schematically illustrated at 112, located at or near the proximal end 124 of system 100. Handle or fixture 112 can incorporate any number of known structures and methods for manipulating and controlling the advancing, withdrawing, positioning and orienting of the various components of system 100, including, but not limited to, guiding member 110, delivery catheter 120, capturing member 140, cutting member 150 and other components and sub-components of system 100, relative to a patient's anatomy and/or relative one another.

Figure 23:
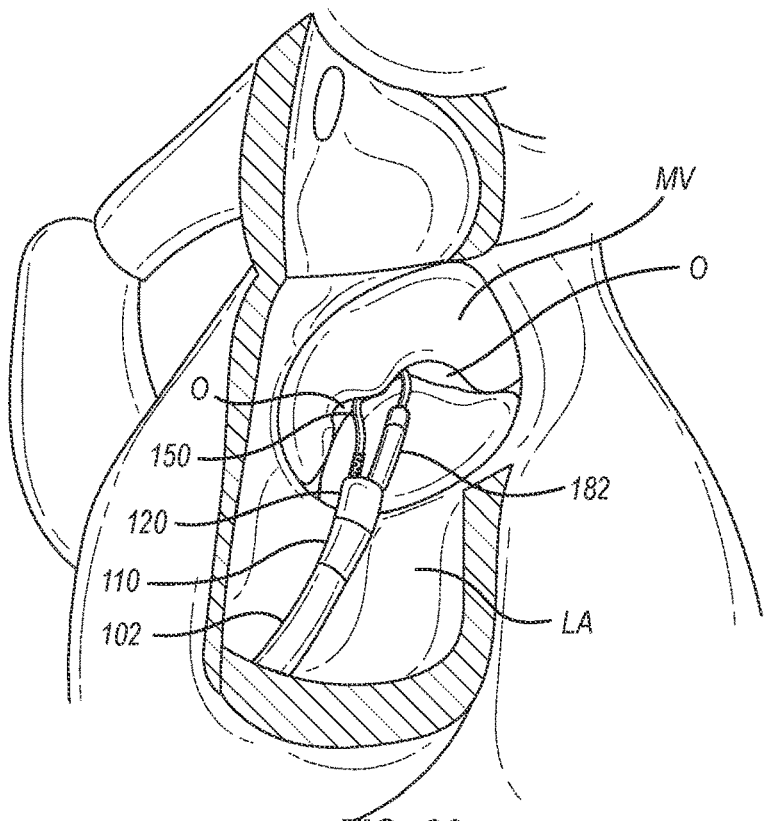
FIG. 23 illustrates a partial cut-away view of a human heart from the left atrium, showing the exposed portion of the cutting member cutting through a portion of one of the leaflets of the mitral valve around the edge-to-edge repair device.
Figure 24:
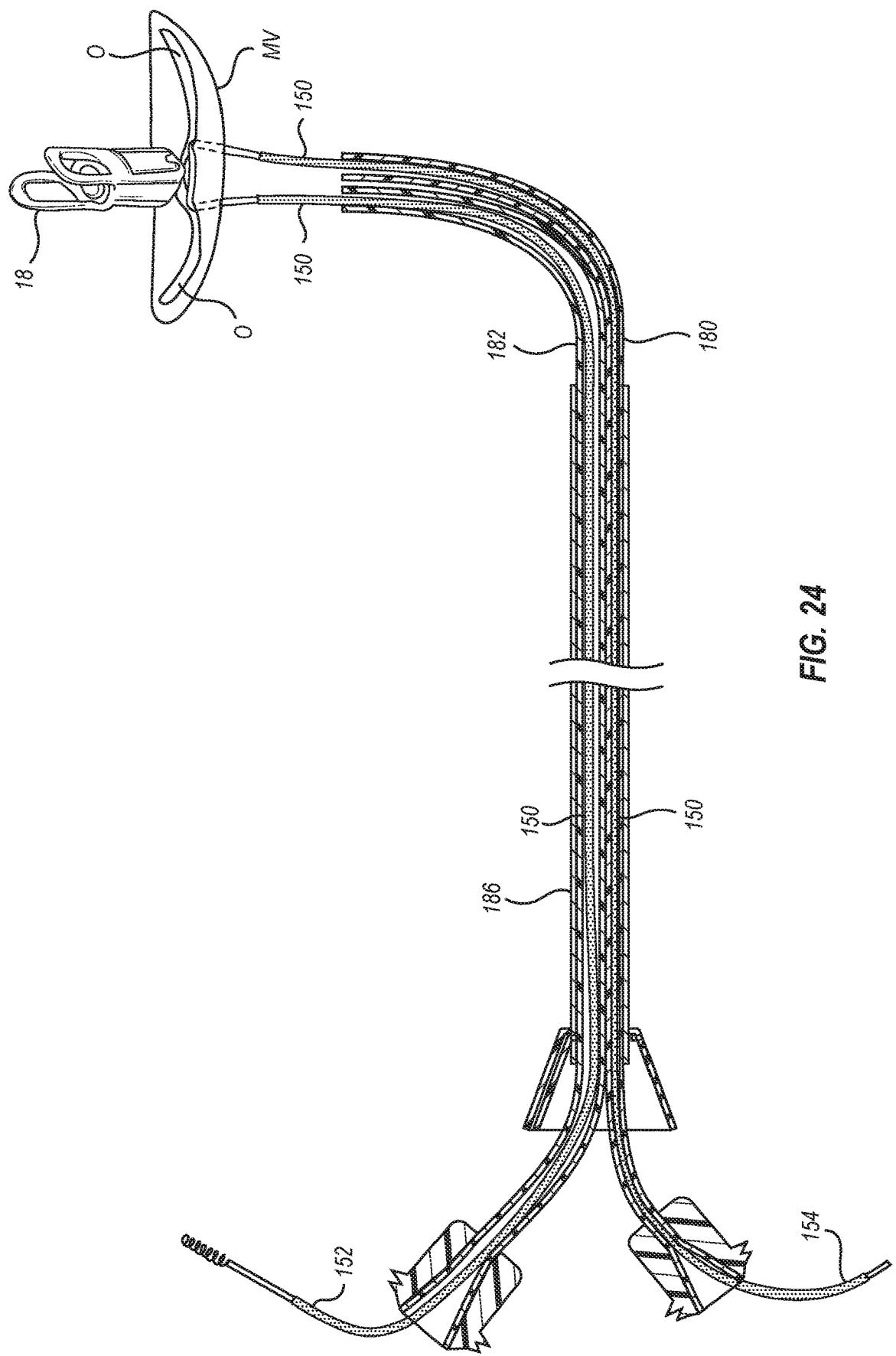
FIG. 24 is a schematic view of the system of FIG. 5, showing one embodiment in which the capture member is withdrawn completely from the device, thereby drawing the cutting member distally through one lumen of the device, around the mitral valve and edge-to-edge repair device, and then back through another lumen of the device in a proximal direction, and thereby positioning an exposed cutting portion formed in the middle of the cutting member at the mitral valve.

FIGS. 6-9 illustrate various possible configurations of the cutting member 150. The cutting members illustrated in FIGS. 6 and 7 enable a full floss technique, wherein the capture member 140, such as a snare, pulls the distal end of cutting member 150 distally out the distal end of one lumen of the delivery catheter, around one of the leaflets of the mitral valve, and then pulls the distal end of the cutting member back through the other lumen of the delivery catheter in a proximal direction until the distal end of the cutting member exits the proximal end of the delivery catheter (as illustrated in FIG. 23). In contrast, the cutting members illustrated in FIGS. 8 and 9 can utilize and keep the capture member 140 in contact with the cutting member 150, only pulling a distal portion of the cutting member 150 around one leaf of the mitral valve and back into distal end of the delivery catheter 120 (as illustrated in FIG. 24). These latter embodiments will allow use of a cutting member having a shorter overall length, making it quicker and easier for the user to manipulate.

Each illustrated cutting member 150a-150d has a proximal end 154a-154d and a distal end 152a-152d. Formed at the distal end 152a-152d is an atraumatic tip 156a-156d that can be formed, in one configuration, from a coil. This atraumatic tip 156a-156d can be shaped by a physician or clinician using the cutting member 150 or can have a preformed shape to aid with positioning the cutting member 150 relative to the edge-to-edge repair device, leaflets, and the orifices O formed by the edge-to-edge repair device and the leaflets. The coil can be formed of a metal or alloy, or other deformable or resiliently deformable material.

Figure 6A:
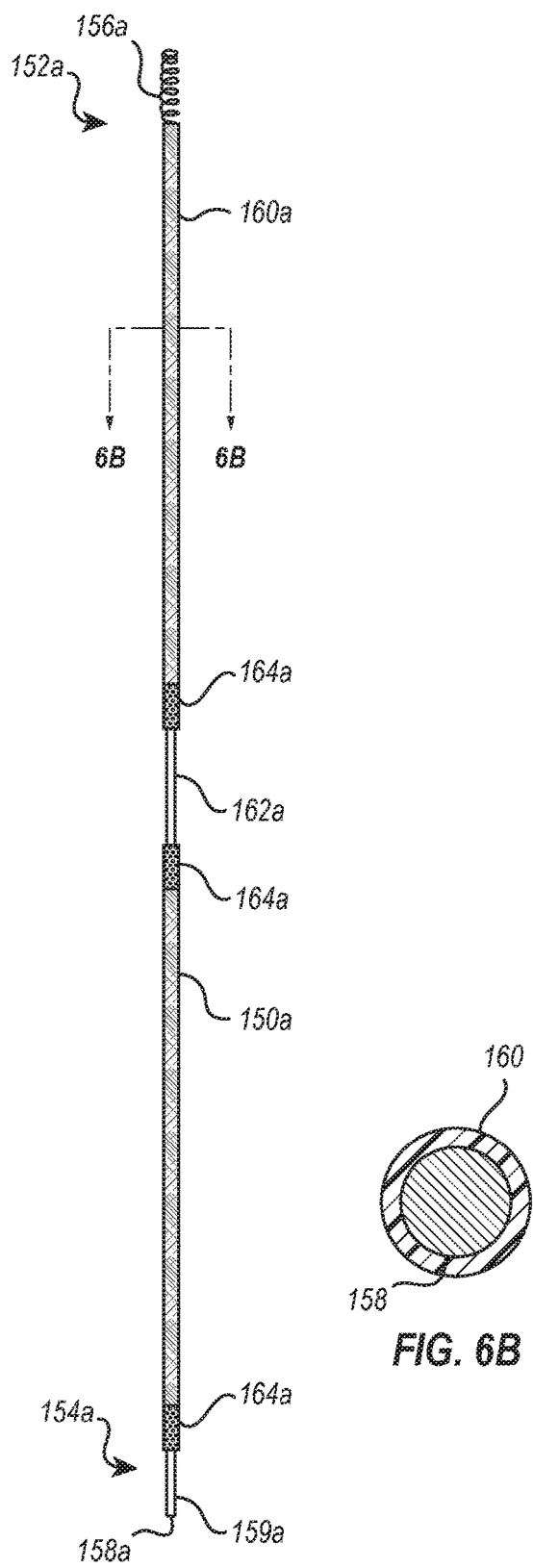
FIGS. 6A and 6B illustrate a cutting member according to one embodiment of the system of FIG. 5.
Figure 6B:
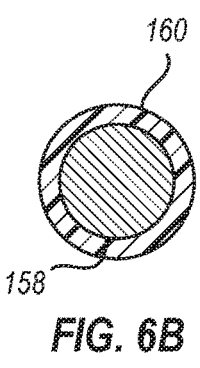
Figure 7:
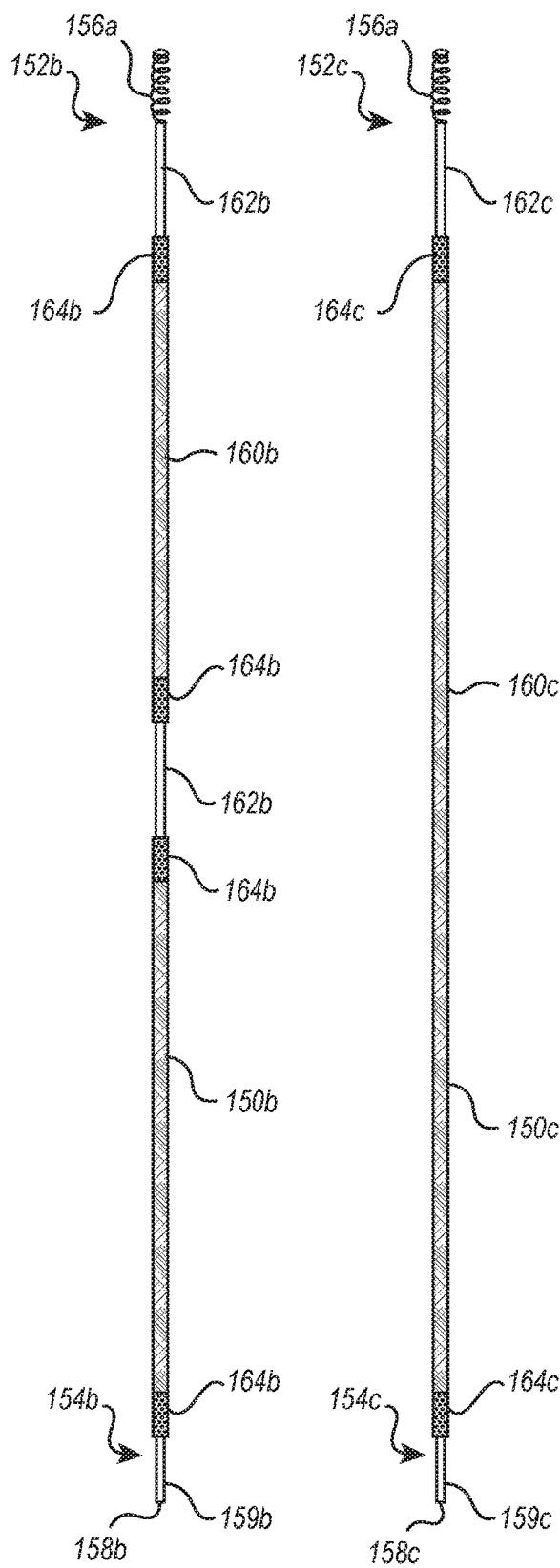
FIG. 7 illustrates a cutting member according to another embodiment of the system of FIG. 5.
Figure 8:
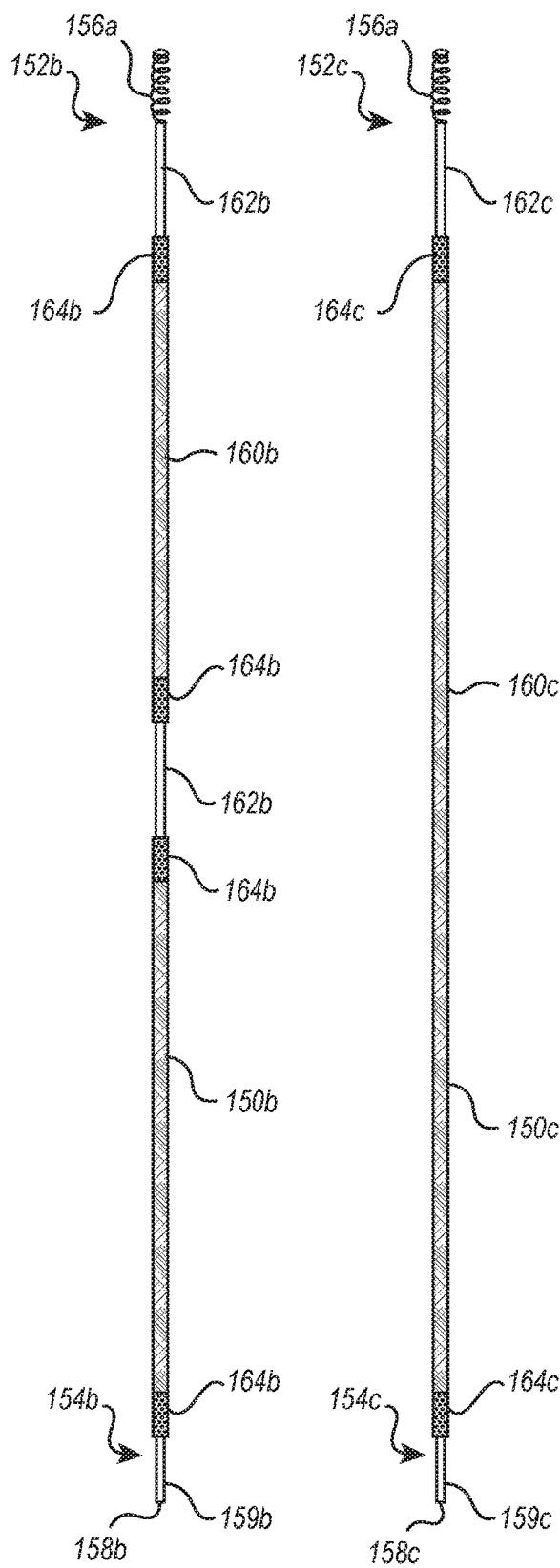
FIG. 8 illustrates a cutting member according to another embodiment of the system of FIG. 5.

Each cutting member 150a-150d has a conductive core 158a-158d and a coating 160a-160d disposed over the conductive core 158a-158d. The coating 160a-160d partially covers the conductive core 158a-158d, except for one or more bare regions 162a-162d where the conductive core 158a-158d is uncoated or exposed. These regions 162a-162d allow radio-frequency energy to be delivered from the conductive core 158a-158d or for such energy to be delivered to tissue contacting those regions 162a-162d to cut, coagulate, desiccate, and fulgurate the tissue. For instance, in FIGS. 6-9 each cutting member 150a-150d includes an uncoated, exposed contact region 159a-159d disposed at respective proximal ends 154a-154d that allow an electrical contact or coupling to be made with electrosurgical device 130. These regions 159a-159d accommodate electrical communication with the electrosurgical device 130. In FIG. 6, an uncoated, exposed cutting region 162a is disposed between the proximal end 154a and the distal end 152a of the cutting member 150a for tissue contact. In FIG. 7, two uncoated, exposed cutting regions 162b are included, one cutting region 162b located near the middle of cutting member 150b and a second cutting region 162b near the distal end 152b of cutting member 150b, again for tissue contact. In FIG. 8, an uncoated, exposed cutting region 162c is provided near the distal end 152c for tissue contact, without a second region disposed between the proximal end 154c and the distal end 152c.

In addition to the conductive core 158a-158d and the coating 160a-160d, each cutting member 150a-150d includes radiopaque markers 164a-164d. These markers 164a-164d define the peripheral bounds of the cutting regions 162a-162d and aid in positioning those regions of the cutting member 150a-150d. For instance, the markers 164a-164d can be viewed via fluoroscopy, x-ray, or other imaging technique. While the markers 164a-164d are illustrated defining the bounds of the cutting regions 162a-162d, other markers can be included to define other locations of the cutting member 150a-150d or any other part of the system 100 or relationship between two or more parts of the system 100.

Figure 9:
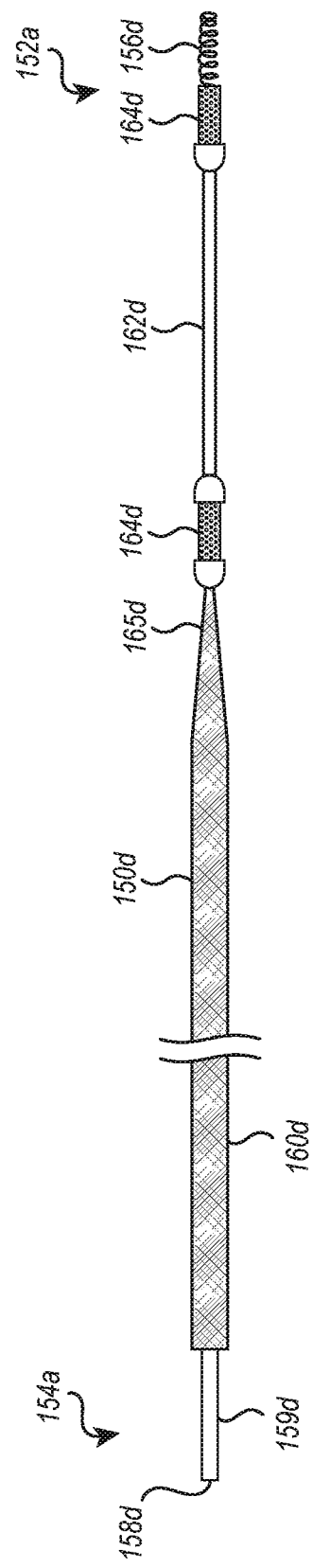
FIG. 9 illustrates a cutting member according to yet another embodiment of the system of FIG. 5.

Referring to FIG. 9, yet another embodiment of cutting member is illustrated, namely cutting member 150d. As with the other embodiments, cutting member 150d can include: an elongate electrically conductive core 158d; an electrically insulative coating 160d covering a large portion of the conductive core 158d; one or more bare, exposed cutting regions 162d; a bare, exposed contact region 159d; one or more radiopaque markers 164d positioned adjacent the cutting region 162d; and an atraumatic tip 156d. In addition, cutting member 150d can include one or more tapered transition regions, such as tapered transition region 165d located between a main body portion of the cutting member 150d and the cutting region 162d.

In one particular embodiment, the electrically conductive core 158d can be made of surgical quality steel and can have a diameter of approximately 0.014" (or approximately 0.04 cm) at its proximal end and a diameter of approximately 0.005" (or approximately 0.01 cm) to approximately 0.008" (or approximately 0.02 cm) in the cutting region(s) 162d. Alternatively, a proximal portion of the cutting member could also be formed from a hypotube. Cutting member 150d can have an overall length of approximately 70" (or approximately 180 cm), with a cutting region 162d of approximately 4" (or approximately 10 cm) in length, and the atraumatic tip can be approximately 0.4" (or approximately 1 cm) to approximately 1.2" (or approximately 3 cm) in length.

The cutting member 150 can be a wire, tubular member, or other elongate structure, with the conductive core being made of a metal, alloy, conductive polymer, or other conductive material. The coating for the cutting member 150 can be a polymer, such as polyterafluoroethylene or other polymer, a hydrophilic coating, a composite material, or other material the can provide lubricity to the cutting member and/or insulative properties to limit unwanted electrical conductivity of the conductive core with the tissue or the other components of the system 100.

Figure 10:
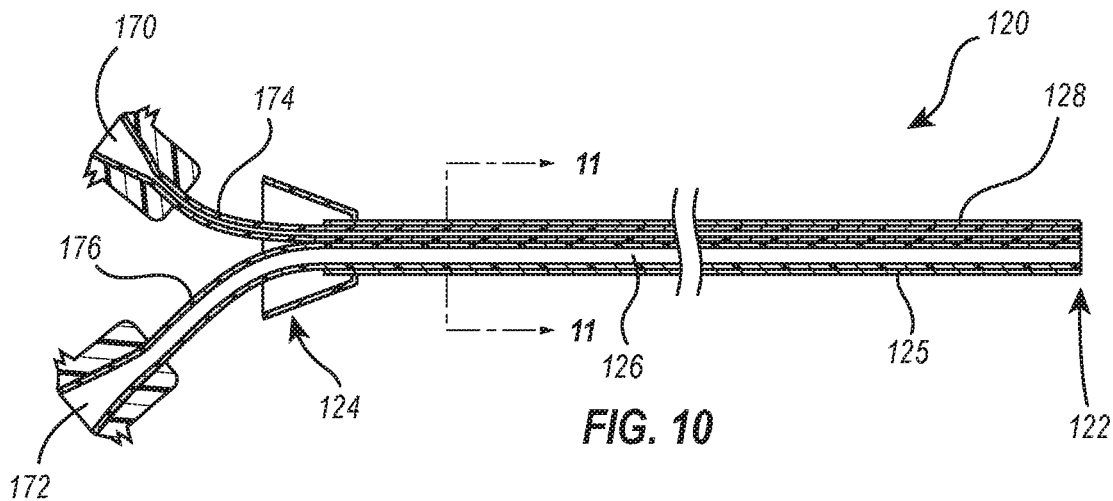
FIG. 10 illustrates a catheter according to one embodiment of the system of FIG. 5.
Figure 15:
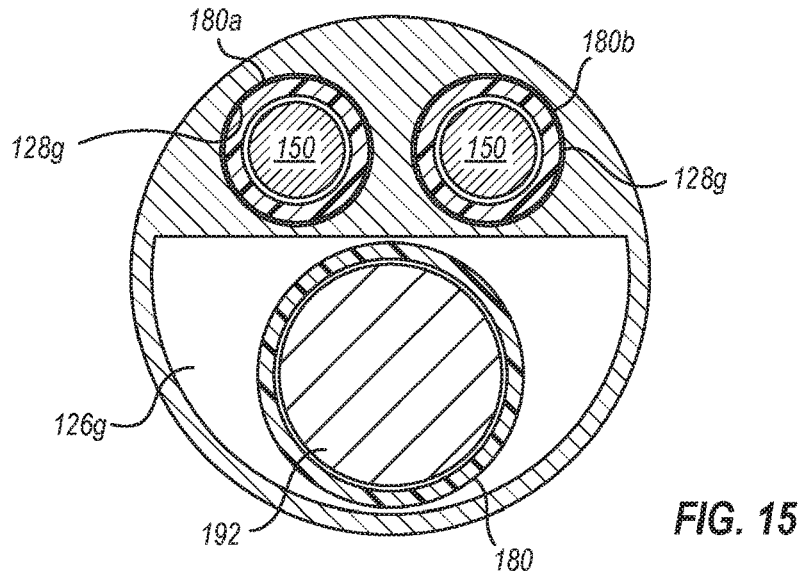
FIG. 15 illustrates another alternate cross-sectional view of yet another embodiment of a catheter of the system of FIG. 5.

Turning to FIG. 10, illustrated is one configuration of the delivery catheter 120. Even though the delivery catheter 120 is depicted straight, one or more resilient, pre-formed bends or curved shapes could be formed at the distal end of delivery catheter 120 to aid in crossing and placing members 140 and 150. Such pre-formed bends or curves can be formed in the distal end portion during extrusion or other fabrication of delivery catheter 120. The delivery catheter 120 can be a microcatheter that is advanceable within a lumen of the guiding catheter 110. To accommodate the capturing member 140 and the cutting member 150, the delivery catheter 120 can have a multi-lumen structure, such as including a lumen 126 that can receive the capturing member 140 and a lumen 128 that can receive the cutting member 150. Alternatively, the delivery catheter can include additional lumens 126 and/or lumens 128, such as illustrated in FIG. 15 and discussed hereinafter.

The lumens 126 and 128 can extend from luer connectors 170 and 172, through extension tubular members 174 and 174, which can join the luer connectors 170 and 172 to a reminder of the delivery catheter 120, to the distal end 122. These lumens 126 and 128 can be formed during extrusion of the shaft 125 of the delivery catheter 120 when the shaft 125 is formed of a polymer or other material capable of being extruded. For instance, FIGS. 10a-10c illustrates different cross-sections for the shaft 125 and different lumen constructions.

Figure 11A:
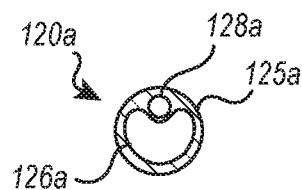
FIGS. 11A-11C illustrate alternate cross-sectional views of the catheter of FIG. 10.
Figure 11B:
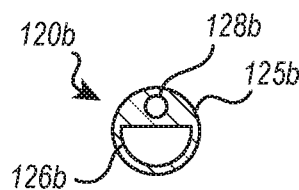
Figure 11C:
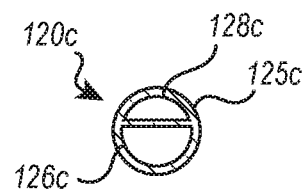

As shown in FIG. 11A, the lumen 126a includes wings that generally surround or extend upwardly to overlap a portion of the lumen 128a in a transverse direction relative to a longitudinal axis of the lumen 128a. In FIG. 11B, the lumen 126b has a generally planar upper surface with a curved bottom surface that approximates the curvature of the shaft 125b. In FIG. 11C, both the lumen 128c and the lumen 126c include curvatures that approximate the curvature of the shaft 125c.

Figure 12A:
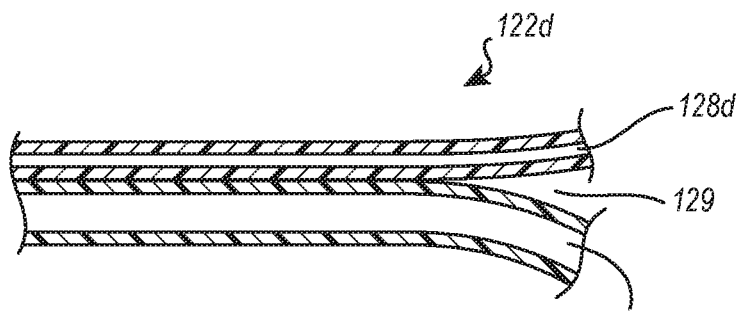
FIGS. 12A and 12B illustrate a catheter according to another embodiment of the system of FIG. 5.
Figure 12B:
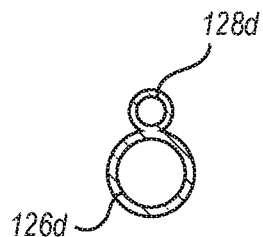

In addition to the shaft 125 and the lumens 126 and 128 having different cross-section, the distal end 122 of the shaft 125 can also have different configurations. For instance, as shown in FIGS. 12A and 12B, the tubular portions of the shaft 125 forming the lumen 126d and 128d can include a cut or slit 129 in the material so that the lumens 126d and 128d, and associated tubular portion, can be spaced apart. This provides for better manipulation of the delivery catheter 120d and better tension during the cutting process. The cross-section of the distal end 122d illustrated in FIG. 12B also aids with enhancing flexibility.

In addition to having the lumens 126 and 128 being formed from the material forming the shaft 125, such as when polymers are assembled to form the shaft 125, it is possible to include separate tubular members that are slidable relative to each other and/or relative to the shaft 125. This provides enhanced positioning capabilities for the delivery catheter 120 because each tubular member is independently advanceable and also independently positionable relative to the distal end 122 of the delivery catheter 120 and the mitral valve MV. Such a structure is illustrated in FIGS. 13, 14 and 15 and is further described below.

Figure 13A:
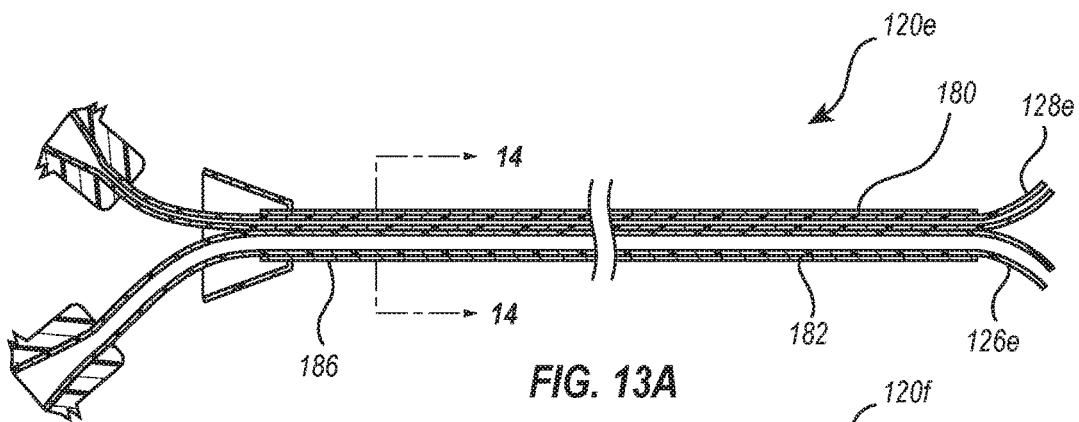
FIG. 13A and 13B each illustrates a catheter according to other embodiments of the system of FIG. 5.

Illustrated in FIG. 13A is one configuration of the delivery catheter 120e. The delivery catheter 120e can be a microcatheter that is advanceable within a lumen of the guiding catheter 110. To accommodate capturing member 140 and cutting member 150, the delivery catheter 120e can also include a first tubular member 180 and a second tubular member 182. In this embodiment, lumens 126e and 128e of delivery catheter 120e can be configured and sized to receive first tubular member 182 and second tubular member 180, respectively. First tubular member 182 can extend through lumen 126e of delivery catheter 120e and terminate at its proximal end in a luer connector 170. The lumen formed within first tubular member 182 can be configured and sized to receive capturing member 140 therethrough. Similarly, second tubular member 180 can extend through lumen 128e of delivery catheter 120e and terminate at its proximal end in a luer connector 172. The lumen formed within tubular member 180 can be configured and sized to receive cutting member 150 therethrough.

The tubular members 180 and 182 can be moved forward and backward, or proximal and distal, relative to a shaft shell 186. Tubular members 180 and 182 can also move axially relative to, and independent of, one another. This allows for enhanced positioning of the distal ends of tubular members 180 and 182 (and, thus, enhanced positioning of capturing member 140 and cutting member 150) relative to the mitral valve MV during the procedure. For instance, the distal end of the tubular member 182 can be closer to the mitral valve MV than the distal end of the tubular member 180 during the procedure, or vice versa, to change the angle at which the looped portion 144 receives the distal end 152 of the cutting member 150. To further enhance the capabilities of the tubular members 180 and 182, one or both can be pre-formed with a resilient, pre-formed shape-memory curve or bend to aid with steerability and positioning of the distal ends of the tubular members 180 and 182 at desired locations within the heart. Thus, the positioning of the delivery catheter 120e and/or the distal ends of the various elements of capturing member 140 and cutting member 150 can be achieved by the steerability of the guiding catheter 110, pre-formed, shape-memory curves or bends in tubular members 180 and 182, or any combination thereof. In addition, a distal portion of the delivery catheter 120e could also be made to be independently steerable once it is advanced beyond the distal end of guiding catheter 110.

Figure 13B:
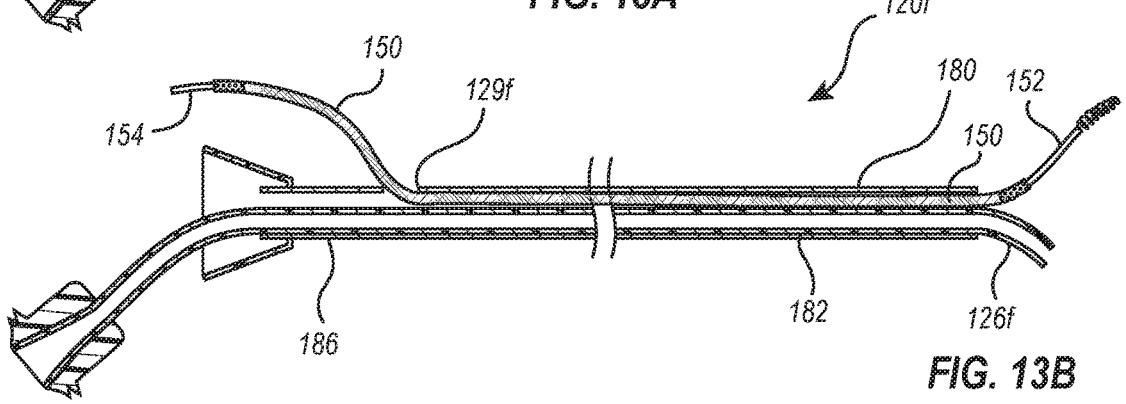

FIG. 13B illustrates yet another embodiment of the delivery catheter 120f that very similar to the embodiment shown in FIG. 13A, except that catheter 120f includes a side port 129f near the proximal end to receive cutting member 150 in a "monorail" or rapid-exchange fashion. This arrangement can simplify the insertion of cutting member 150 into the delivery catheter 120f and can also allow the overall length of cutting member to be shortened.

Figure 14A:
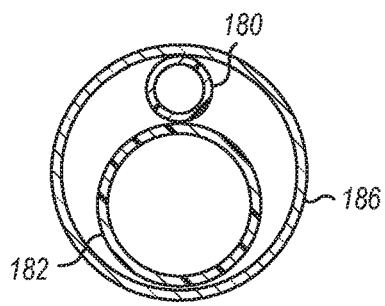
FIGS. 14A and 14B illustrate alternate cross-sectional views of the catheter of FIG. 13.
Figure 14B:
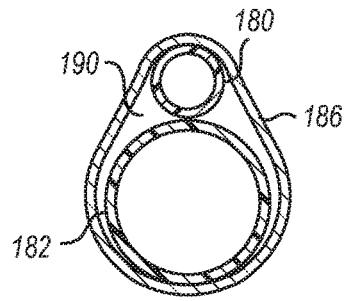

Alternatively, as illustrated in FIGS. 14A and 14B, delivery catheter 120a can be take the form of a simple outer shell 186 that surrounds tubular members 180 and 182 (without providing separate lumens, such as lumens 126e and 128e). The shell 186 can have a fixed shape, such as illustrated in FIG. 14A or can have a flexible form that approximates an outer surface profile of the tubular members 180 and 182, as shown in FIG. 13B. In FIG. 14B, while the shell 186 generally approximates the outer surface profile of the tubular members 180 and 182, spaces can be formed between the shell 186 and the tubular member 180 and 182, such as spaces 190. Varying a durometer of the polymer or material forming the shell 186 allows for the different configurations.

Generally, the shaft and other portions of the delivery catheters 120 can be fabricated from polymers, metals, alloys, combinations thereof, or other materials that can accommodate the manufacture of the delivery catheter.

Illustrated in FIG. 15 is another cross-sectional configuration of the delivery catheter described herein. As mentioned above, the delivery catheters 120 described herein can include multiple lumens, with those lumens accommodating or receiving either the capture member 140 and the cutting member(s) 150 directly or including tubular members, such as tubular members 180a, 180b and 182, that accommodate or receive the capture member 140 and the cutting members 150a and 150b.

The delivery catheter 120g of FIG. 15 can include 3 lumens: lumen 126g and two lumens 128g. Disposed within each of the lumens 128g is a tubular member 180a and 180b) (similar to the tubular member 180 described in reference to FIGS. 12 and 13), which can receive two separate cutting members 150a and 150b. Disposed within the lumen 126g is a needle 192, which can be used to puncture the septum and, optionally, leaflet tissue or tissue adjacent to the leaflets to allow passage of the capture member 140 through a leaflet or other tissue. Once used to puncture the leaflet or other tissue, the needle 192 can be removed and the capture member 140, whether alone or with the tubular member 182, can be advanced through the lumen 126g. This configuration allows the delivery device 120g to accommodate two cutting members 150a and 150b that can be used to cut tissue either sequentially or simultaneously.

The system 100 can be used to position the delivery catheter 120 in various spaces within a patient's anatomy. For instance, and as will be described herein, the system 100 can be used to position the capturing member 140 and the cutting member 150 relative to leaflets in apposition to an edge-to-edge repair device, such as the MitraClip® or a suture "bow-tie." However, the presently described system 100 and associated methods and devices can be used for other valvular structures or other tissues in an anatomy.

Figure 16:
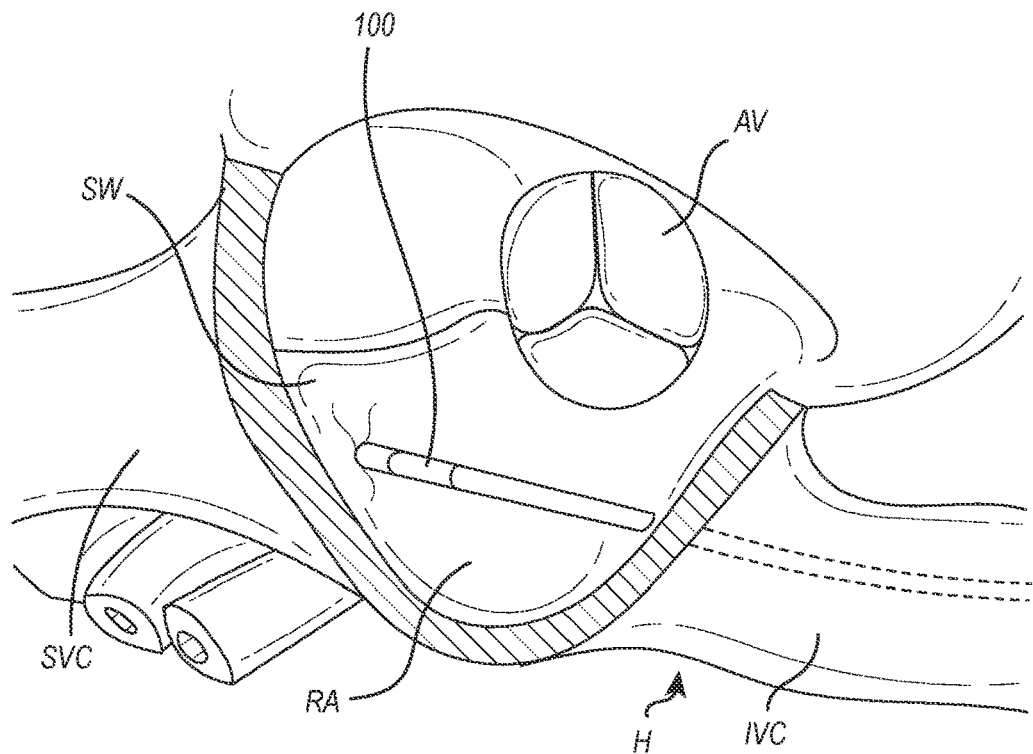
FIG. 16 illustrates a partial cut-away view of a human heart, showing a distal portion of the leaflet cutting device inserted into the right atrium and into the septal wall.
Figure 17:
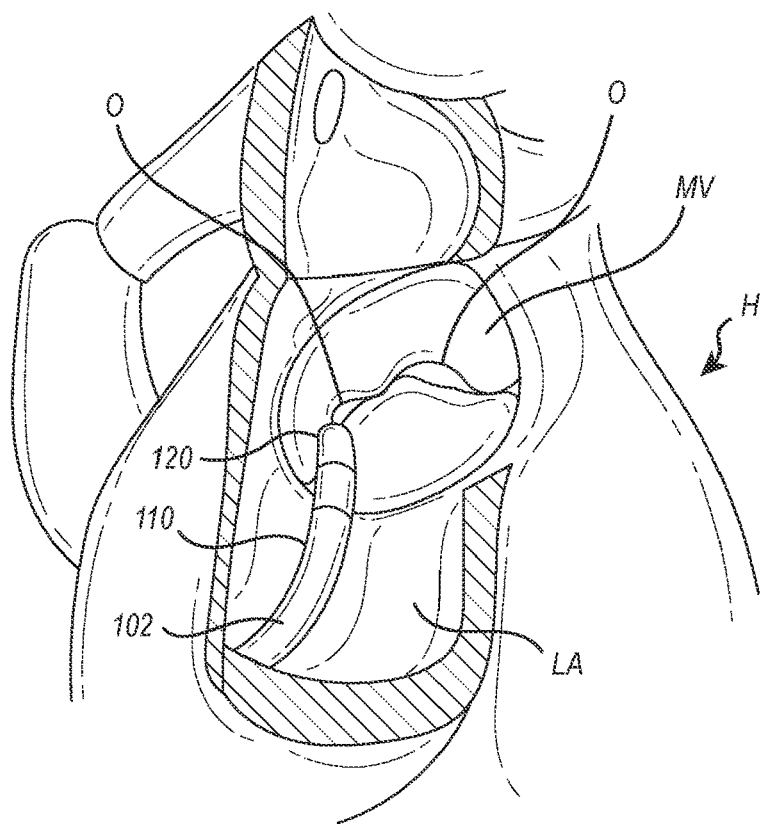
FIG. 17 illustrates a partial cut-away view of a human heart, showing a distal portion of the leaflet cutting device after having passed through the septal wall into the left atrium of the heart and having been steered toward and positioned adjacent the mitral valve.

The positioning and deployment of the leaflet cutting device is more particularly illustrated in FIGS. 16-23. In use, the guiding catheter 110 can access the left atrium LA from the femoral artery using the inferior vena cava as illustrated in FIG. 16. Following a trans septal puncture using an appropriately placed needle advanced through a lumen of the guiding catheter, the guiding catheter 110 is introduced into the left atrium as illustrated in FIG. 17. Once positioned in the left atrium, the steerability of guiding catheter 110 is used to direct the distal end of delivery catheter 120 toward and adjacent to the mitral valve as further shown in FIG. 17. In other words, the guiding catheter 110 can be steered toward the mitral valve (MV) so that the center of the guiding catheter 110 is substantially centered on the previously implanted edge-to-edge repair device. This can include generally aligning a longitudinal axis of the guiding catheter 110 toward the edge-to-edge repair device (not shown). Once in place, the delivery catheter 120 can be advanced along the lumen in preparation for deployment.

With an end of the guiding catheter 110 facing the edge-to-edge repair device, the distal ends of lumens 126 and 128 can be positioned through orifices 0 on either side of edge-to-edge repair device. For instance, where the embodiment shown in FIG. 12A is employed, the shaft of the delivery catheter 120 can be advanced so that the lumen 126d and the lumen 128d can each be advanced into a separate orifice located to either side of the edge-to-edge repair device, i.e., the lumen 126d extends through one orifice O and the lumen 128d extends through the other orifice O. Similarly, when the delivery catheter 120e or the delivery catheter 120f is deployed from the guiding catheter 120, the tubular members 180 and 182 are advanced into and through orifices O on either side of the edge-to-edge repair device so that the tubular member 180 is in one orifice O and the tubular member 182 is in the other orifice O as illustrated in FIGS. 18A and 18B.

Figure 20:
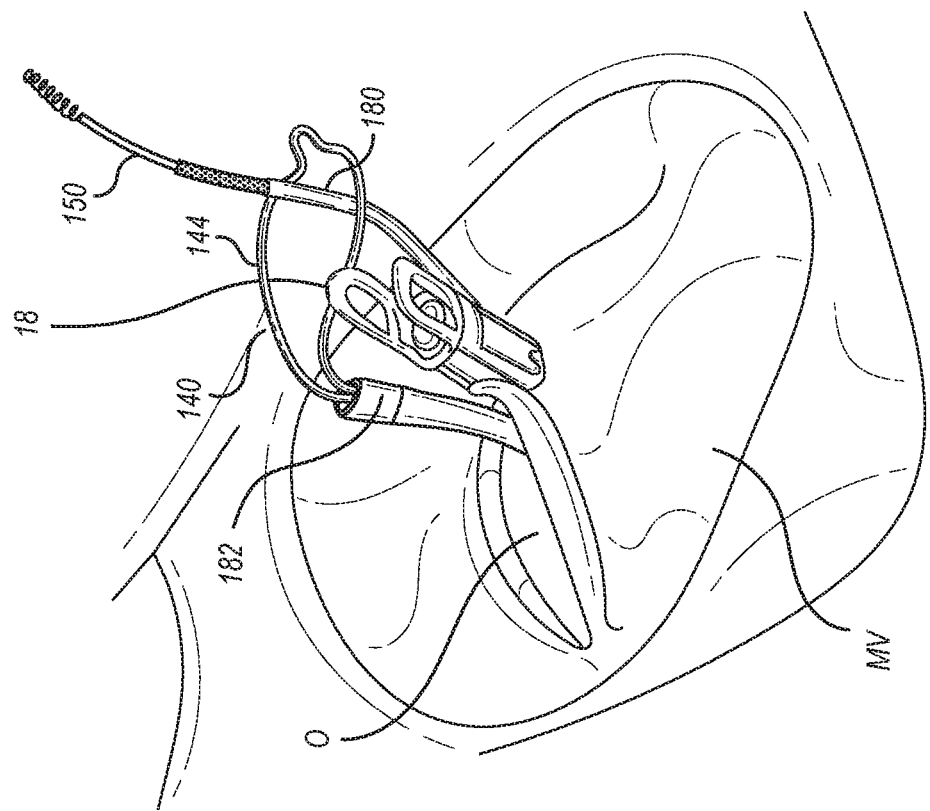
FIG. 20 illustrates a partial cut-away view of a human heart from the left ventricle, showing the cutting member having been advanced through the snare loop of the capturing member.
Figure 19:
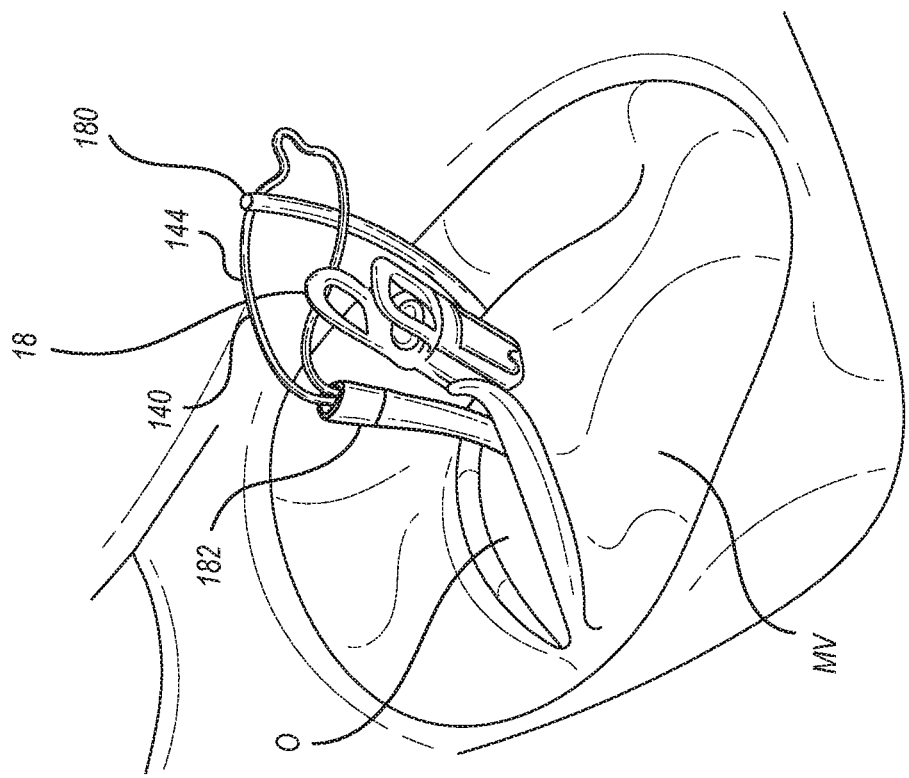
FIG. 19 illustrates a partial cut-away view of a human heart from the left ventricle, showing a shape-memory snare loop having been deployed from the capturing member in preparation for capturing the cutting member.
Figure 21:
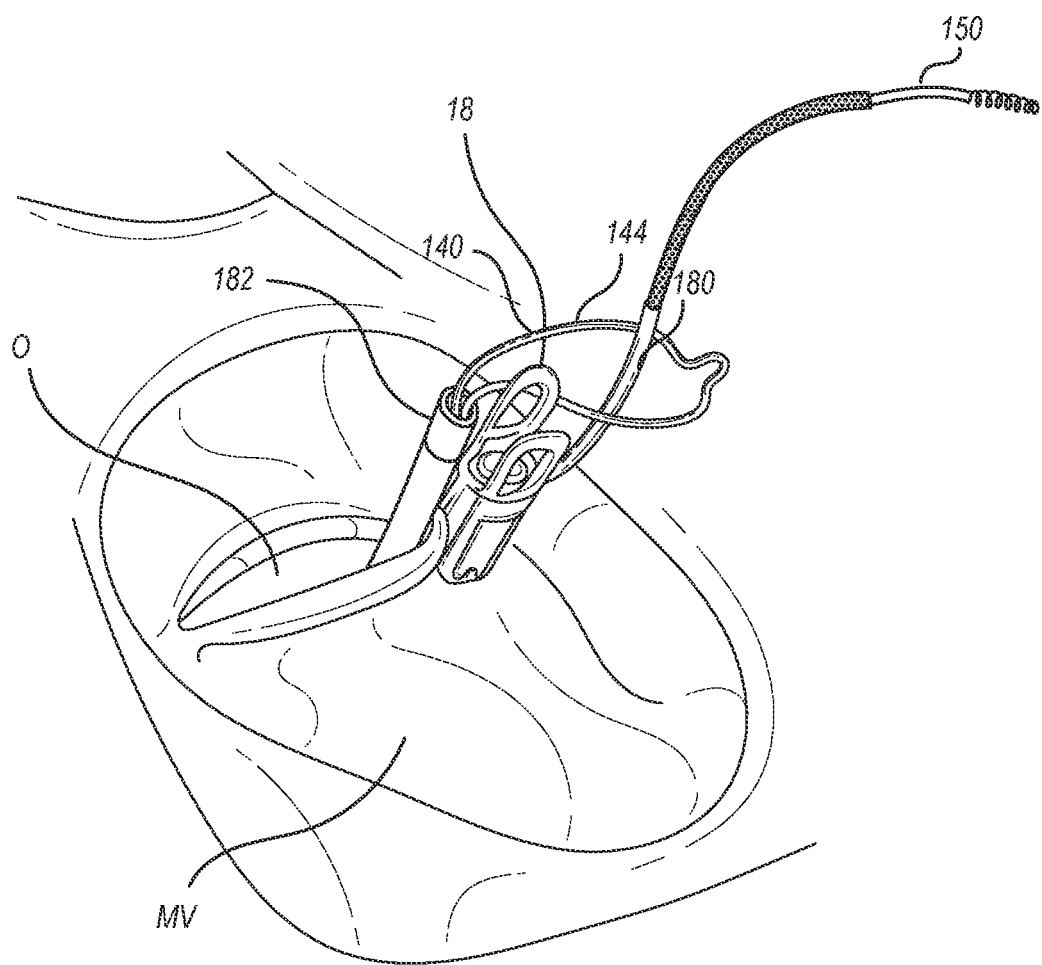
FIG. 21 illustrates a partial cut-away view of a human heart from the left ventricle, showing the snare loop being withdrawn back into the capturing member, thereby contacting and capturing the cutting wire.

With the delivery catheter 120 so positioned, the capture member 140 can be advanced from the lumen 128 (and from the tubular member 182) into the left ventricle. By so doing, the looped portion 144 can self-expand to form a ring or opening (as shown in FIG. 19) with which to receive the cutting member 150. As the cutting member 150 is advanced from the lumen 128 (and from the tubular member 180), it is captured by the looped portion 144 as shown in FIG. 20. The tubular members 180 and 182 can also be independently moved to help position the distal ends of the lumens 126 and 128. As mentioned above radiopaque markers can be provided at different locations around the looped portion 144, as well as at various locations on the distal end portion of the cutting member 150, to assist in locating and visualizing the relative locations, positions and orientation of such components relative to one another.

Figure 22A:
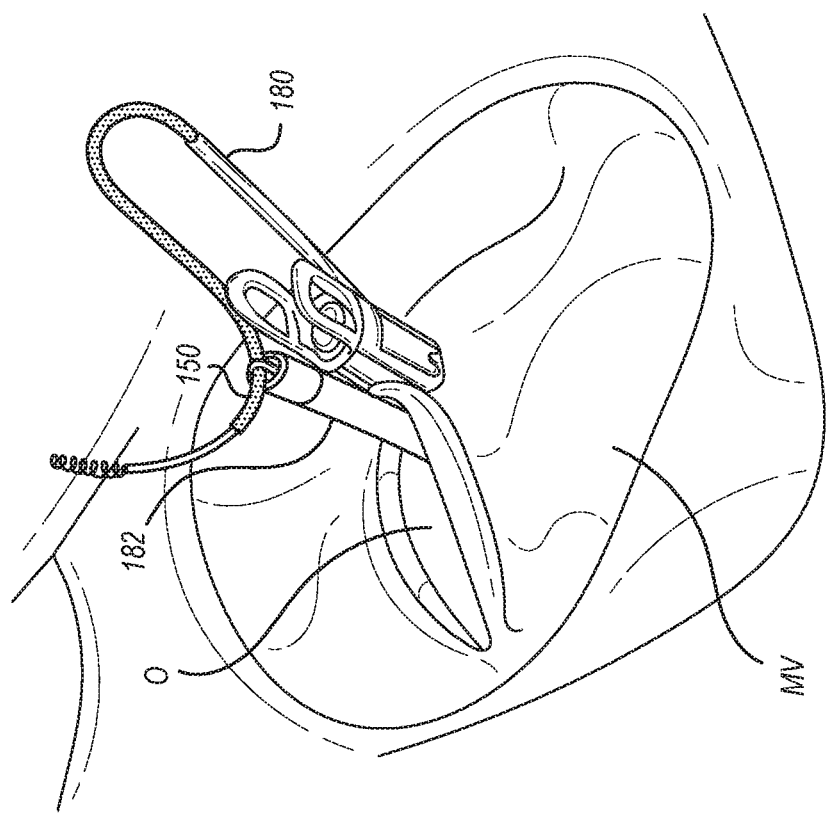
FIGS. 22A-22C illustrate partial cut-away views of a human heart from the left ventricle, showing the snare being progressively withdrawn back into the capturing member so as to position an exposed portion of the cutting member in position preparatory for cutting a portion of the leaflet of the mitral valve adjacent the edge-to-edge repair device.
Figure 22B:
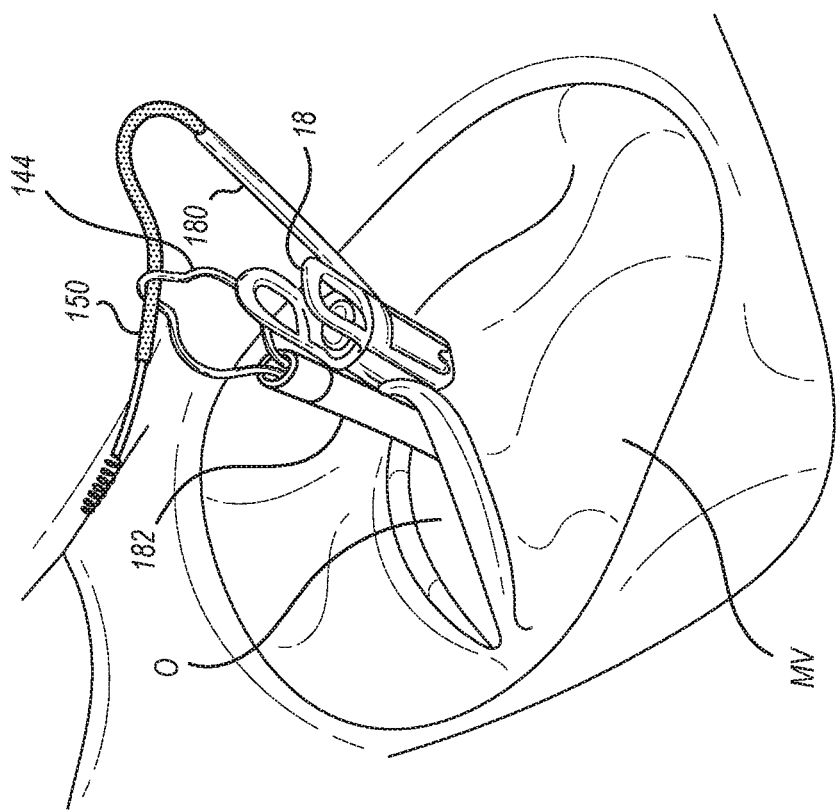
Figure 22C:
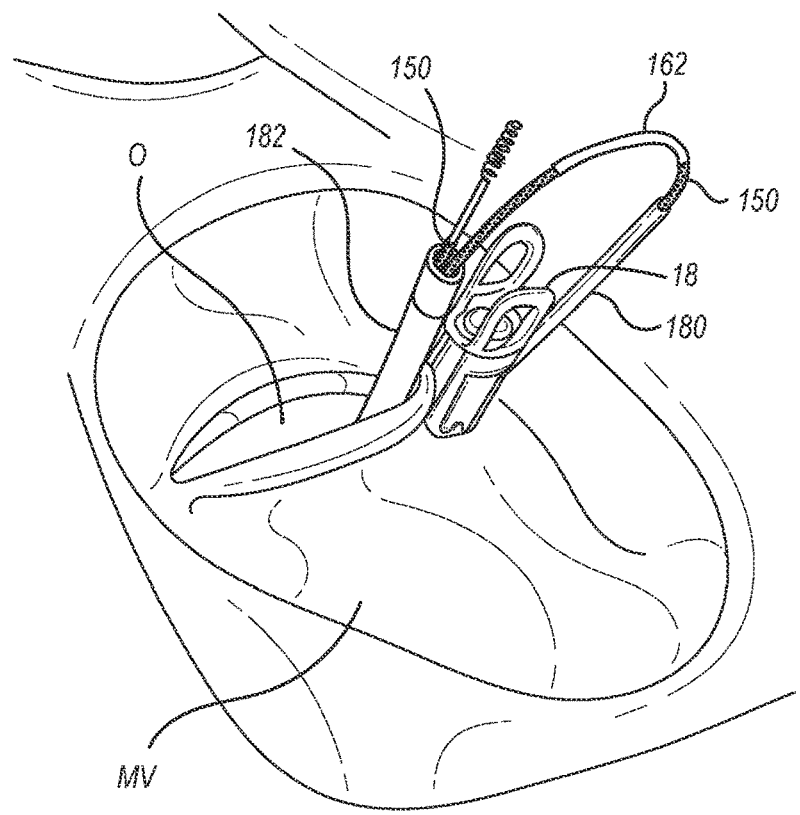

When the position of the cutting member 150 is verified through comparing the location of the radiopaque markers 164 against radiopaque markers formed on the proximal and distal ends of the looped portion 144, the capture member 140 can be withdrawn towards the deliver catheter 120, and the lumen 126 as illustrated in FIG. 22. Optionally, the cutting member 150 can also be advanced in a distal direction at the same time to form a loop in the cutting member 150 and/or vary a length of available cutting member to contact the leaflet that will be cut. The pushing of the cutting member 150 and pulling of the capture member 140 can position the cutting member 150, and more particularly, the bare cutting regions 162 in the desired leaflet location as shown in FIGS. 22A-22C.

Following positioning of the cutting member 150, the leaflet can be cut by applying electrical energy to the cutting member 150 and drawing the exposed cutting regions 162 through the leaflet tissue, as illustrated in FIG. 23, thereby detaching the edge-to-edge repair device from one of the leaflets while remaining attached to the other leaflet. Thereafter, the physician or clinician can then perform one or more of a mitral valve annuloplasty, balloon valvuloplasty, mitral valve repair, installation of a replacement valve, and combinations thereof.

FIG. 24 is a schematic view of the system of FIG. 13A, showing one embodiment (sometimes referred to herein as a "full floss" embodiment) in which the capture member 140 can be completely withdrawn from the device. In this embodiment, the capture member 140 is withdrawn in a proximal direction, thereby drawing the distal end of cutting member 150 distally through one lumen of the device (such as lumen 128), around the mitral valve and edge-to-edge repair device, and then back through the other lumen of the device (such as lumen 126) in a proximal direction, thereby positioning an exposed cutting region 162 formed in the middle of the cutting member 150 at the mitral valve. In addition, this allows for both uncoated ends 159 and 162 of the cutting member to be accessible at the proximal end of the device for connection to the electrosurgical device 130 and thereby form an electrical circuit for the passage of electrosurgical energy. In this embodiment, the capturing member 140 is completely withdrawn from the delivery catheter 120 in order to deploy and position the cutting member 150.

Figure 25:
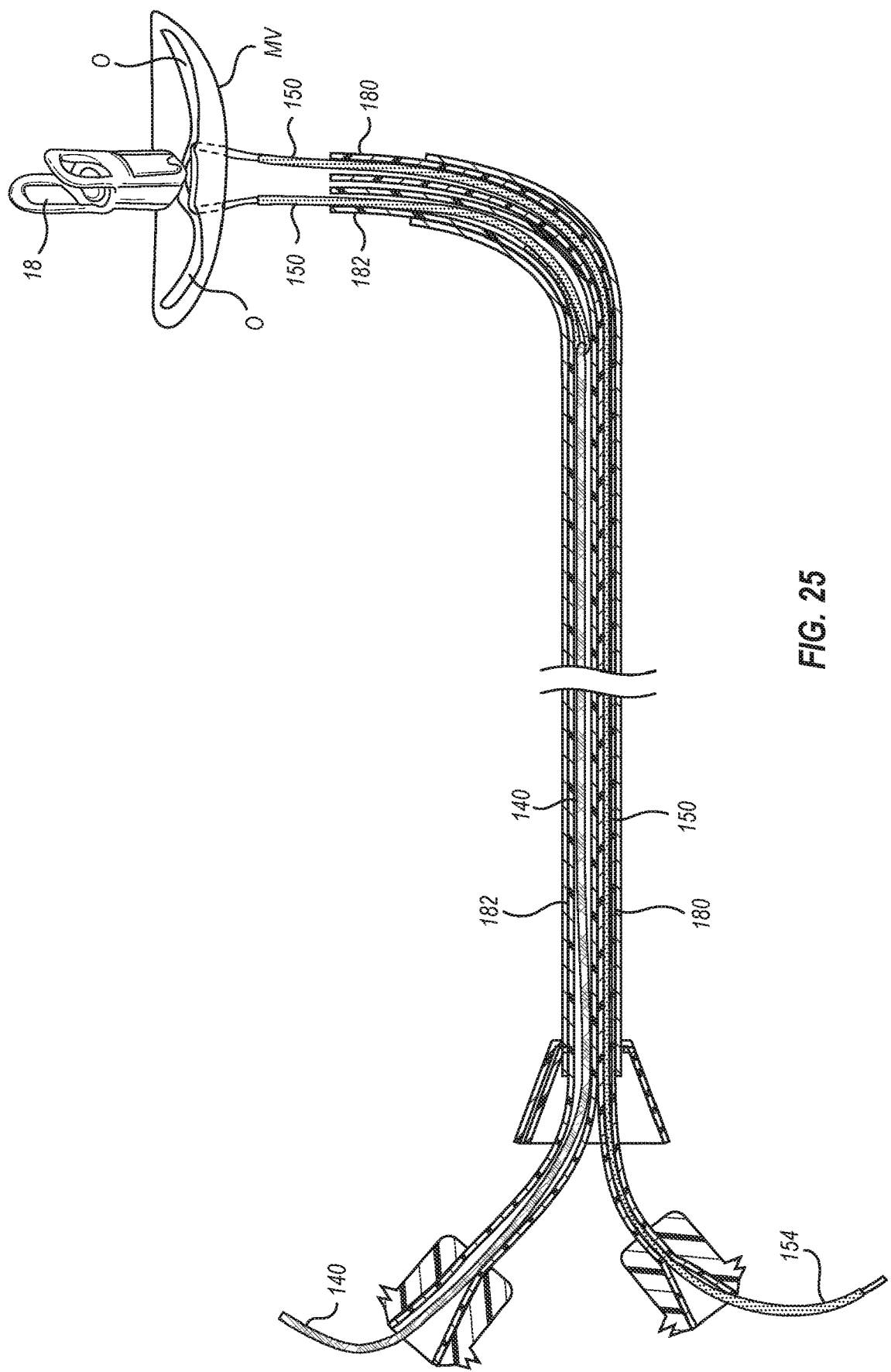
FIG. 25 is a schematic representation of the system of FIG. 5, showing another embodiment in which the capture member is partially withdrawn in a proximal direction, thereby drawing a distal end portion of the cutting member around the mitral valve and edge-to-edge repair device, and thereby positioning an exposed cutting portion formed proximately the distal end of the cutting member.

FIG. 25 is a schematic representation of the system of FIG. 13A, showing another embodiment in which the capture member 140 is only partially withdrawn in a proximal direction to position an exposed cutting portion 162 formed near a distal end portion of the cutting member 150 around the mitral valve and edge-to-edge repair device. With this embodiment, the overall of length of the capture member 140 can be shorter than that required with the embodiment of FIG. 24. However, this embodiment may require the use of a patient return electrode in order to complete the electrical circuit, since only one end of the cutting member is accessible at the proximal end of the device for connection to the electrosurgical device 130.

In an alternate approach, schematically illustrated in FIGS. 26A-26D, instead of capturing the distal end 152 of the cutting member 150 to position the cutting member 150, the cutting member 150 can be advanced through the leaflet as a puncturing tool without capturing or positioning with the capture member 140. For instance, a combination of puncturing and cutting the leaflet with the cutting member 150 and lassoing either with the capture member 140 or another lasso advanced through another lumen of the delivery catheter 120 can used to (i) puncture the leaflet, (ii) capture a portion of the edge-to-edge repair device, (iii) cut one leaflet, (iv) capture another portion of the edge-to-edge repair device, and (v) cut the other leaflet before removing the edge-to-edge repair device. This would allow for removal or at least partial detachment of multiple edge-to-edge repair devices from one or more leaflets.

Figure 26A:
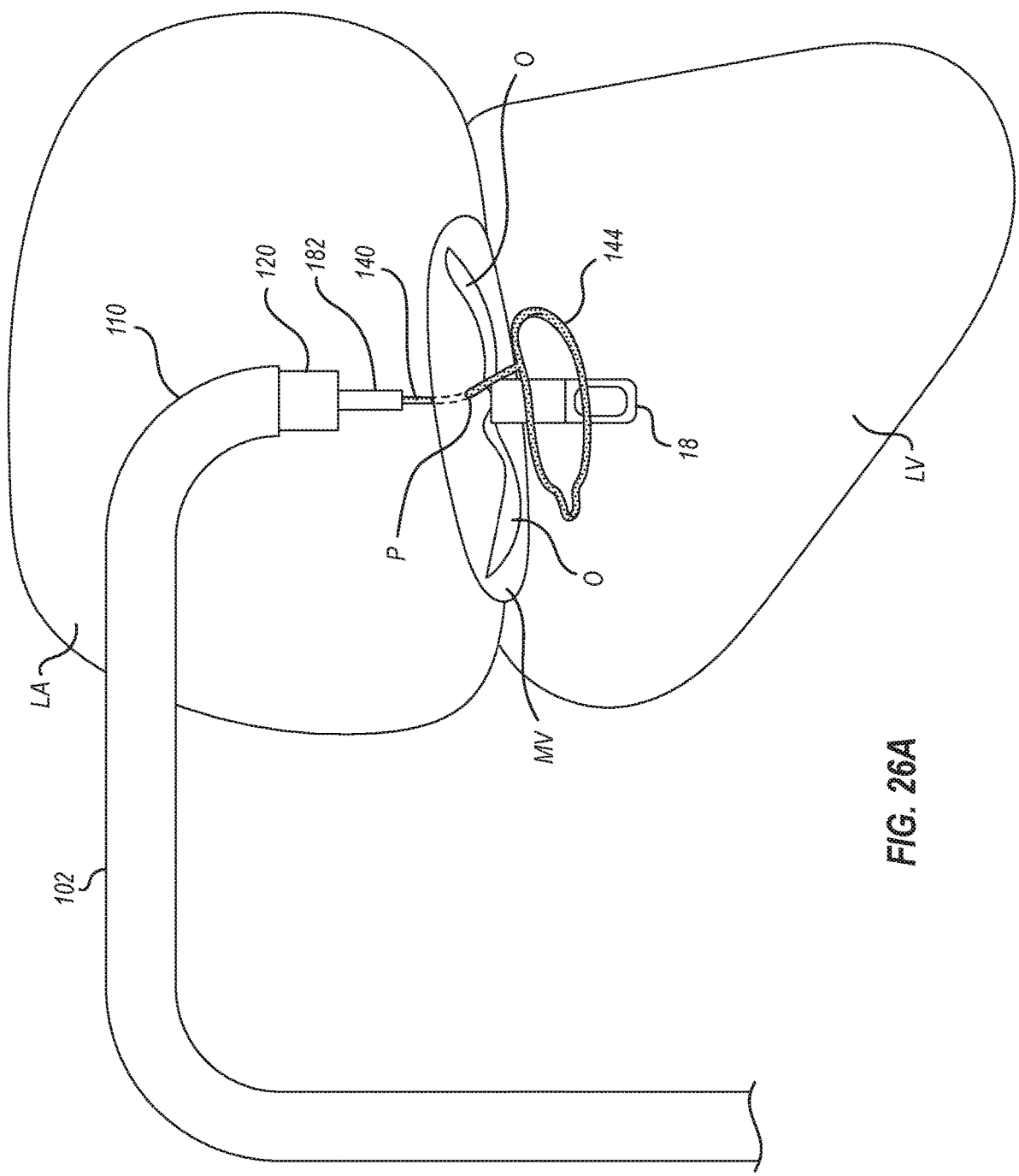
FIGS. 26A-26D are schematic representations of yet another embodiment of the system of FIG. 5, in which a puncture is made in one of the leaflets of the mitral valve, the capturing member is inserted through the puncture, two separate cutting members are passed through the orifices located on opposite sides of the edge-to-edge repair device, which are then captured by the snare loop of the capturing member and then drawn proximally back into the capturing member so as to place exposed cutting portions of each cutting wire in position to cut portions of the leaflet around the edge-to-edge repair device.

This alternate approach, using the delivery catheter 120f, is schematically illustrated in FIGS. 26A-26D. With an end of the delivery catheter 120f facing the edge-to-edge repair device 18, the needle 192 can be advanced through the tissue of one of the leaflets, such as from a distal end of the tubular member 182, to create a puncture P through the tissue of one of the mitral valve leaflets and positioned adjacent the edge-to-edge repair device 18. Once the puncture is formed, the needle 192 is removed and the capture member 140 (and/or the lumen 126 containing capture member 140) is advance through the puncture P in the leaflet tissue and into the ventricle. Alternatively, the delivery catheter 120f can be advanced over the needle 192 and through the puncture to position a distal end of the delivery catheter 120f in a desired position to deploy the capture member 140. In still another configuration, the tubular member 182 is sized to accommodate the needle 192, and when the needle 192 is removed, receives the capture member 140. Telescoping the tubular member 182 over the needle 192, once it has punctured the tissue, can place the distal end of the lumen 126f in the ventricle so the capture member 140, once the needle 192 is removed and the capture member 140 is disposed within the lumen 126f, can be deployed from the lumen 126f into the desired location for capturing the cutting member 150, as shown in FIG. 26A.

Figure 26B:
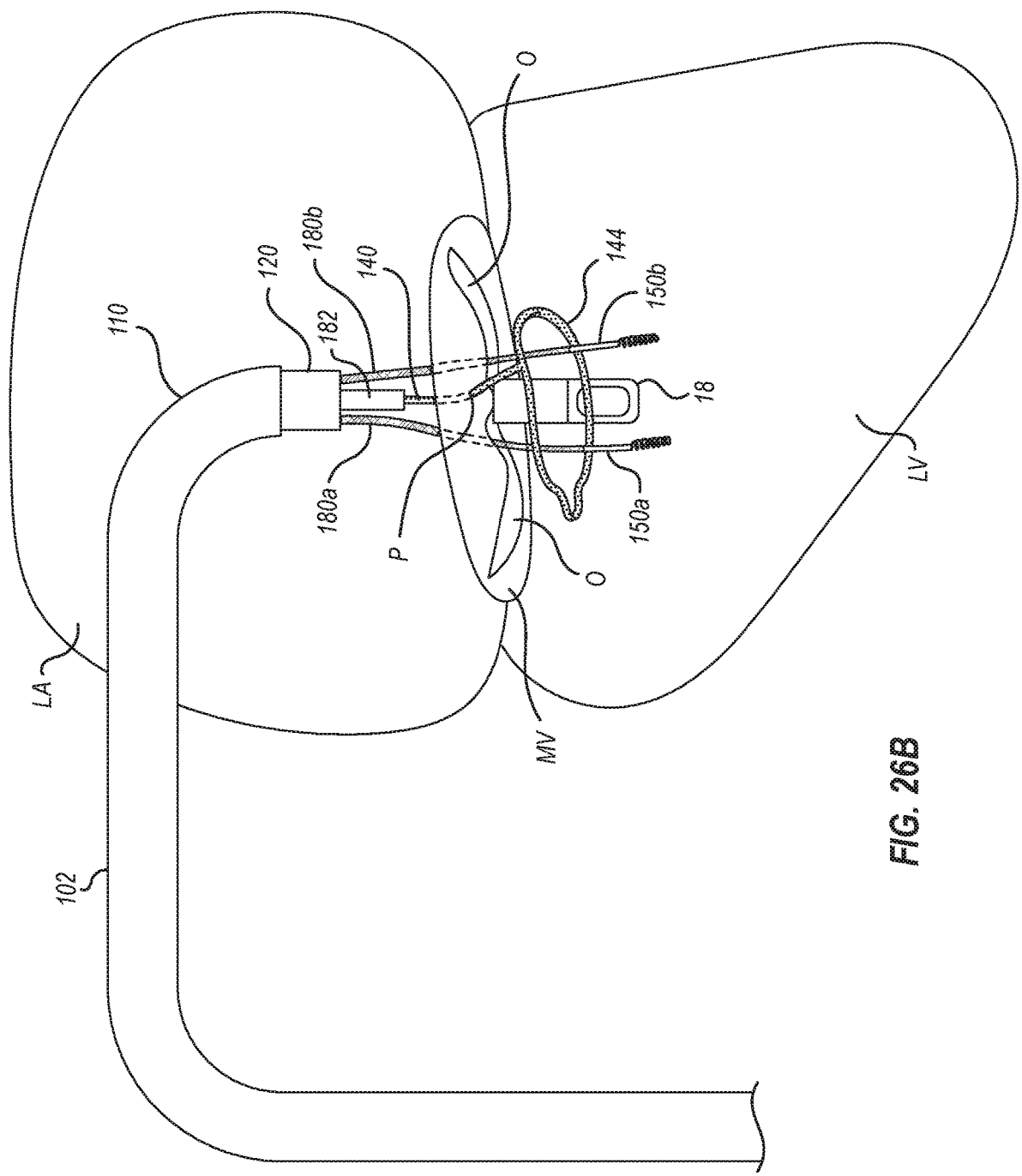

With the capture member 140 in place, i.e., the looped portion 144 self-expands to form a ring or opening with which to receive the cutting members 150a and 150b, the two tubular members 180a and 180b are advanced to position the distal ends of tubular members 180a and 180b through orifices O on either side of the edge-to-edge repair device 18, as shown in FIG. 26B. The distal ends of the cutting members 150a and 150b are in position for deployment so they might be advance into the looped portion 144. The tubular members 180a, 180b and 182 can be moved together or independently to position the distal ends of the lumens 126f and 128f. Alternatively, any grouping of the tubular members 180a, 180b and 182 can be moved together. For example, the tubular members 180a and 180b can be moved together, while independently from the tubular member 182. Any combination of movement of the tubular members 180a, 180b and 182 is possible.

Figure 26C:
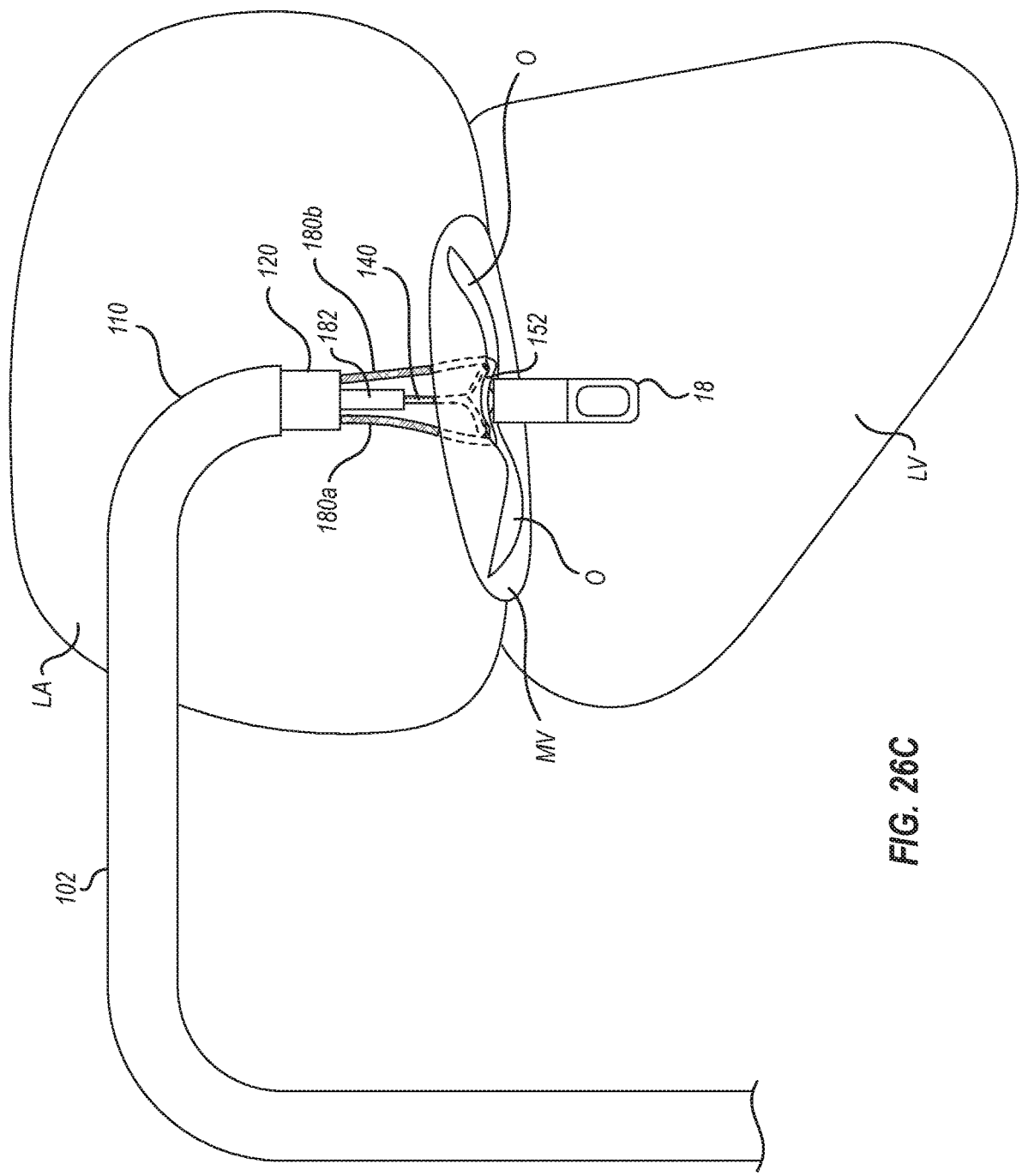
Figure 26D:
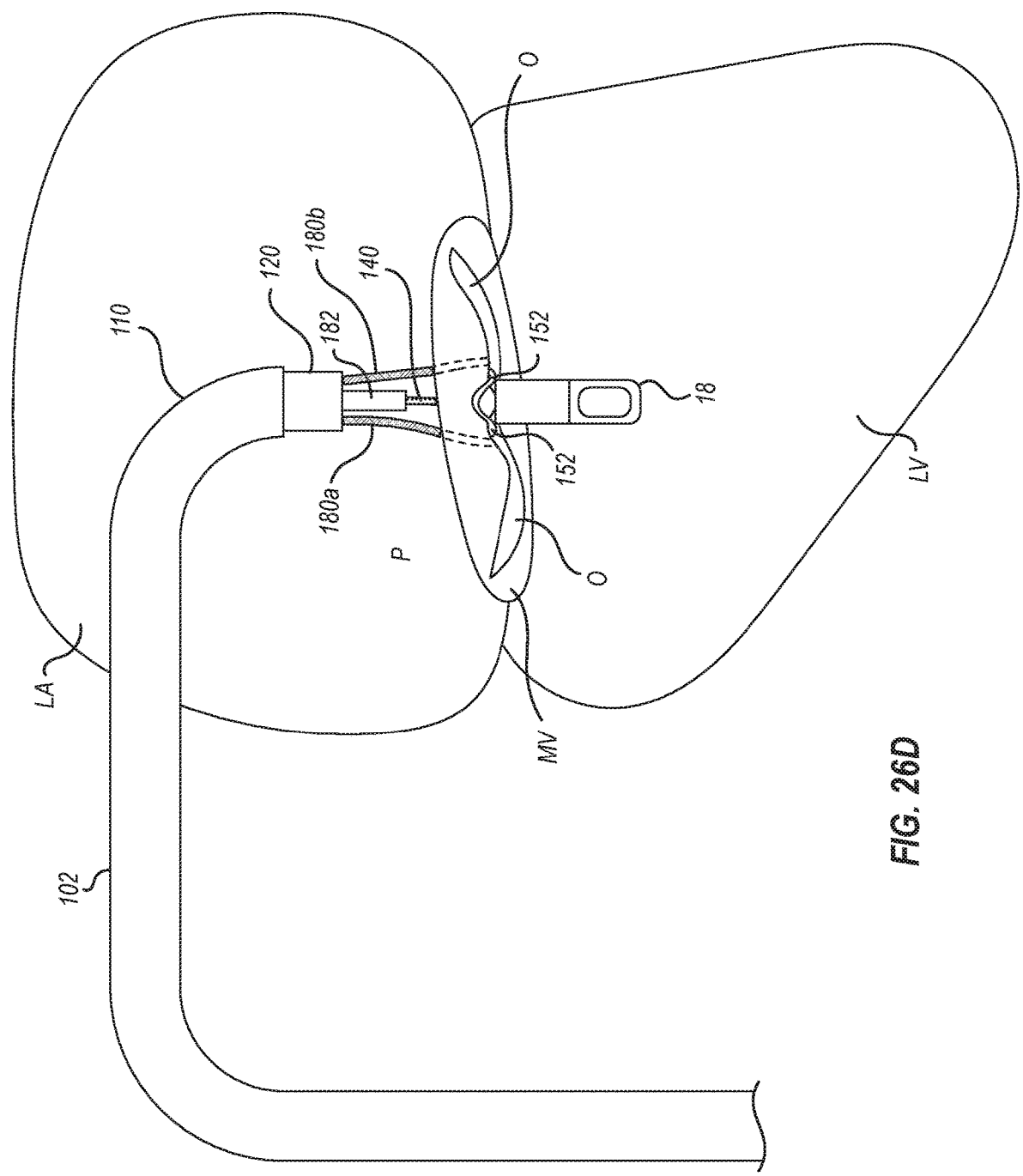

When the position of the cutting members 150a and 150b are verified through comparing the location of the radiopaque markers 164 against radiopaque markers formed on the proximal and distal ends of the looped portion 144, the capture member 140 can be withdrawn towards the deliver catheter 120, and the lumen 126, as shown in FIG. 26C. As capture member is withdrawn into tube 182, distal end portions of cutting members 150a and 150b are drawn through their respective orifices O, around the tissue separating each orifice and the puncture P and then pass into the distal end of lumen 126 of tube 182, as shown in FIG. 26D. Optionally, the cutting members 150a and/or 150b can be advanced to vary a length of available cutting member to contact the leaflet that will be cut. The pushing of the cutting members 150a and/or 150b and the pulling of the capture member 140 can position the cutting members 150a and 150b, and more particularly, the bare regions 162a and 162b in the desired leaflet location. In any event, once the exposed cutting regions of cutting members 150a and 150b are in the desired positions, the leaflet can then be cut by applying electrical energy to the cutting members 150a and 150b and drawing the exposed cutting regions 162 through the leaflet tissue located between each orifice O and puncture P. Alternatively, the tubular members 180a and 180b can optionally be moved to selectively isolate or insulate the tissue from the cutting member(s) 150. For instance, the tubular member 180a can be advanced to isolate or insulate the tissue, such as leaflet tissue, from the cutting member 150a, while the cutting member 150b is used to cut the tissue (i.e., the cutting member 150b is energized to cut the tissue). Thereafter, the tubular member 180a is retracted to expose the cutting member 150a and the tubular member 180b is advanced to isolate or insulate the tissue from the cutting member 150b, and then cutting member 150a can be energized to cut the tissue.

Once the edge-to-edge repair device 18 is successfully detached from a first one of the leaflets, then a physician or clinician can move onto performing other procedures. Alternatively, if it is desirable or necessary to completely remove the edge-to-edge repair device 18, delivery catheter 120*f* can also be used to sequentially cut the edge-to-edge repair device 18 from both leaflets of the mitral valve. In other words, delivery device 120*f* can first be deployed in the manner discussed above to cut one leaflet and then be subsequently deployed in a similar manner to cut the other leaflet. In either event, the physician or clinician can then move on to perform one or more of a mitral valve annuloplasty, balloon valvuloplasty, mitral valve repair, installation of a replacement valve, and combinations thereof.

The technology described and claimed herein could also be readily adapted to selectively target and cut tissue in other areas of the human anatomy via similar endovascular procedures.

In keeping with the foregoing embodiments and disclosure, the technology disclosed herein can be directed to systems, devices and methods for at least partially detaching an edge-to-edge repair device that holds together anterior and posterior leaflets of a mitral valve of a human heart. For example, the devices are directed to at least partially detaching an edge-to-edge repair device that holds together anterior and posterior leaflets of a mitral valve of a human heart and can include one or more of the following elements: an elongate member having a proximal end, a proximal end portion, a distal end portion and a distal end, the elongate member; a guiding catheter with a distal end portion that can be selectively bent to reorient the distal end portion of the elongate member; a delivery catheter coaxially located within the guiding catheter; a delivery catheter shell having a first lumen and a second lumen, each extending from a proximal end to a distal end of the delivery catheter shell; a first tubular member having a distal end portion and positioned within the first lumen and being moveable in an axial direction relative to the delivery catheter shell; a second tubular member having a distal end portion and positioned within the second lumen and being moveable in an axial direction relative to the delivery catheter shell; a capture member extending through the first tubular member and being movable in an axial direction relative to the first tubular member, the capture member having a self-expanding, shape-memory loop formed at a distal end thereof; and/or a first cutting member extending through the second tubular member and being movable in an axial direction relative to the second tubular member, the first cutting member comprising an electrically conductive core extending its entire length, an electrically insulative coating covering a major portion of the conductive core, and one or more uncoated, electrically conductive cutting regions. The devices can also include one or more of the following additional features: wherein one or both of the first and second tubular members include a preferential, shape-memory bend in the distal end portion thereof; wherein the cutting member comprises a first cutting region and a second cutting region, wherein the first cutting region is disposed at a proximal end of the cutting member and the second cutting region is disposed between the proximal end and a distal end of the cutting member; wherein the first cutting region is disposed at and forms a distal end of the cutting member, proximal of an atraumatic coil tip; wherein the cutting member further comprises one or more radiopaque markers defining peripheral bounds of the cutting regions; wherein the capture member comprises a self-expanding, shape-memory loop portion for capturing the cutting member; wherein the loop portion comprises a narrowed portion configured to facilitate preferential collapsing of the capture member upon drawing the capture member into the second tubular member; and/or wherein the capture member further comprises one or more radiopaque markers defining peripheral bounds of the loop portion.

Similarly, the methods can be directed to at least partially detaching an edge-to-edge repair device that holds anterior and posterior leaflets of the mitral valve together, wherein a first orifice in the mitral valve is located to one side of the edge-to-edge repair device and a second orifice in the mitral valve is located to an other side of the edge-to-edge repair device, and can include, for example, any one or more of the following steps or acts: advancing a capture member from a first catheter portion that extends from a distal end of a delivery catheter and through the first orifice; advancing a cutting member from a second catheter portion that extends from the distal end of the delivery catheter and through the second orifice; capturing the cutting member with the capture member and positioning the cutting member around a portion of one of the leaflets of the mitral valve adjacent to the edge-to-edge repair device; and/or cutting at least a portion of one of the leaflets adjacent to the edge-to-edge repair device to detach the edge-to-edge repair device from the at least one of the anterior or posterior leaflets.

In another embodiment, the methods can include any one or more of the following steps or acts: advancing an elongate member through a least a portion of the vasculature of a patient and into a left atrium of a patient's heart, the elongate member having a proximal end portion, distal end portion and a distal end, the proximal end portion being located and accessible outside the patient's vasculature, the elongate member having a guiding catheter with a distal end portion that can be selectively bent to reorient the distal end portion of the elongate member, the elongate member also having a delivery catheter coaxially located within the steering catheter, the delivery catheter having a first lumen and a second lumen, each extending from a proximal end to a distal end of the delivery catheter, the delivery catheter also having a capture member extending through the first lumen and cutting member extending through the second lumen; puncturing, with the distal end of the elongate member, a septal wall between the right atrium and a left atrium of the heart and advancing the distal end portion of the elongate member into the left atrium of the heart; bending the distal end portion of the steering catheter to direct the distal end portion of the elongate member toward the mitral valve and align the delivery catheter with the edge-to-edge repair device; advancing the capture member beyond the distal end of the delivery catheter and through the first orifice; advancing the cutting member beyond the distal end of the delivery catheter and through the second orifice; capturing a distal end portion of the cutting member with a distal end portion of the capture member; withdrawing the distal end portion of the capture member in a proximal direction through the first lumen to position a cutting region formed in the cutting member around a portion of one of the anterior or posterior leaflets of the mitral valve adjacent to the edge-to-edge repair device; and/or applying electrical energy to the cutting member to cause the cutting region to cut through a portion of the tissue of one of the anterior and posterior leaflets adjacent to the edge-to-edge repair device to detach the edge-to-edge repair device from the at least one of the anterior or posterior leaflets.

Further still, the methods can also include any one or more of the following additional steps or acts: advancing a distal end portion of the capture member beyond a distal end of the first catheter portion, the distal end portion of the capture member having a self-expanding, shape-memory loop, and allowing the self-expanding, shape-memory loop to deploy on a ventricular side of the mitral valve; advancing a distal end portion of the cutting member beyond a distal end of the second catheter portion and through the loop of the capturing member; withdrawing the capturing member in a proximal direction and causing the loop to snare the cutting member and draw it around the edge-to-edge repair device and into contact with a portion of the tissue of the leaflet between the first and second orifices and adjacent to the edge-to-edge repair device; withdrawing the capture member in a proximal direction until one of the electrically conductive cutting regions passes around and is positioned against the tissue of the leaflet adjacent the edge-to-edge repair device; advancing the cutting member in a distal direction to aid in positioning one of the electrically conductive cutting regions against the tissue of the leaflet adjacent the edge-to-edge repair device; applying electrical energy to the cutting member; positioning the first catheter portion in the first orifice and positioning the second catheter portion in the second orifice; positioning the first catheter portion in the first orifice by sliding the first catheter portion within a body of the delivery catheter; positioning the second catheter portion in the second orifice by sliding the second catheter portion within a body of the delivery catheter; positioning the first catheter portion independently of positioning a second catheter portion; positioning the first catheter portion relative to the second catheter portion by moving the first catheter portion away from the second catheter portion; positioning the first catheter portion relative to the second catheter portion, wherein the first catheter portion and the second catheter portion are formed at the distal end of the delivery catheter, the delivery catheter comprising a split portion that allows the first catheter portion to extend away from the second catheter portion; performing a procedure selected from the group consisting of mitral valve annuloplasty, balloon valvuloplasty, mitral valve repair, installation of a replacement valve, and combinations thereof; and/or withdrawing the snare into the second catheter portion while advancing the cutting member from the first catheter portion to vary a length of the cutting member exposed to the anterior and posterior leaflets.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of at least partially detaching an edge-to-edge repair device that holds anterior and posterior leaflets of the mitral valve together, wherein a first orifice in the mitral valve is located to one side of the edge-to-edge repair device and a second orifice in the mitral valve is located to another side of the edge-to-edge repair device, the method comprising:

advancing an elongate member through at least a portion of the vasculature of a patient and into a left atrium of a patient's heart, the elongate member having a proximal end portion, a distal end portion, and a distal end, the proximal end portion being located outside the patient's vasculature, the elongate member receiving a delivery catheter having a first catheter lumen and a second catheter lumen, each extending from a proximal end to a distal end of the delivery catheter, the delivery catheter also having a capture member extending through the first catheter lumen and a cutting member extending through the second catheter lumen;

advancing a capture member from a-the first catheter lumen of the elongate member that extends from a distal end of a delivery catheter and through the first orifice;

advancing a cutting member from a-the second catheter lumen of the elongate member that extends from the distal end of the delivery catheter and through the second orifice, wherein a distal end of the cutting member includes an atraumatic coil tip;

capturing the cutting member with the capture member and positioning the cutting member around a portion of one of the leaflets of the mitral valve adjacent to the edge-to-edge repair device; and cutting at least a portion of one of the leaflets adjacent to the edge-to-edge repair device to detach the edge-to-edge repair device from the at least one of the anterior or posterior leaflets, wherein a distal end of the delivery catheter comprises a split portion that allows the first catheter lumen to extend away from the second catheter lumen.

2. The method of claim 1, wherein the act of advancing the capture member further comprises advancing a distal end portion of the capture member beyond a distal end of the first catheter lumen, the distal end portion of the capture member having a self-expanding, shape-memory loop, and allowing the self-expanding, shape-memory loop to deploy on a ventricular side of the mitral valve.

3. The method of claim 2, wherein the act of advancing the cutting member further comprises advancing a distal end portion of the cutting member beyond a distal end of the second catheter lumen and through the loop of the capturing member.

4. The method of claim 3, wherein the step of capturing the cutting member further comprises withdrawing the capturing member in a proximal direction and causing the loop to snare the cutting member and draw it around the edge-to-edge repair device and into contact with a portion of the tissue of the leaflet between the first and second orifices and adjacent to the edge-to-edge repair device.

5. The method of claim 4, wherein the cutting member includes one or more electrically conductive cutting regions positioned at one or more discrete locations along its length, and wherein the act of positioning the cutting member further comprises withdrawing the capture member in a proximal direction until one of the electrically conductive cutting regions passes around and is positioned against the tissue of the leaflet adjacent the edge-to-edge repair device.

6. The method of claim 5, wherein the act of positioning the cutting member further comprises advancing the cutting member in a distal direction to aid in positioning one of the electrically conductive cutting regions against the tissue of the leaflet adjacent the edge-to-edge repair device.

7. The method of claim 6, wherein the act of cutting at least a portion of one of the leaflets further comprises an act of applying electrical energy to the cutting member.

8. The method of claim 1, further comprises positioning the first catheter lumen relative to the second catheter lumen by moving the first catheter lumen away from the second catheter lumen.

9. The method of claim 1, further comprises positioning the first catheter lumen relative to the second catheter lumen, and wherein the first catheter lumen and the second catheter lumen are formed at the distal end of the delivery catheter.

10. The method of claim 1, further comprising performing a procedure selected from the group consisting of mitral valve annuloplasty, balloon valvuloplasty, mitral valve repair, installation of a replacement valve, and combinations thereof.

11. The method of claim 1, wherein capturing the cutting member with the capture member and positioning the cutting member in proximity with the edge-to-edge repair device comprises withdrawing a snare into the second catheter lumen while advancing the cutting member from the first catheter lumen to vary a length of the cutting member exposed to the anterior and posterior leaflets.

12. A method of at least partially detaching an edge-to-edge repair device that holds anterior and posterior leaflets of the mitral valve together, wherein a first orifice in the mitral valve is located on one side of the edge-to-edge repair device and a second orifice in the mitral valve is located on another side of the edge-to-edge repair device, the method comprising:
  advancing an elongate member through at least a portion of the vasculature of a patient and into a left atrium of a patient's heart, the elongate member having a proximal end portion, a distal end portion, and a distal end, the proximal end portion being located and accessible outside the patient's vasculature, the elongate member having a guiding catheter with a distal end portion that can be selectively bent to reorient the distal end portion of the elongate member, the elongate member also having a delivery catheter coaxially located within the guiding catheter, the delivery catheter having a first lumen and a second lumen, each extending from a proximal end to a distal end of the delivery catheter, the delivery catheter also having a capture member extending through the first lumen and a cutting member extending through the second lumen;
  puncturing, with the distal end of the elongate member, a septal wall between the right atrium and a left atrium of the heart and advancing the distal end portion of the elongate member into the left atrium of the heart;
  bending the distal end portion of the guiding catheter to direct the distal end portion of the elongate member toward the mitral valve and align the delivery catheter with the edge-to-edge repair device;
  advancing the capture member beyond the distal end of the delivery catheter and through the first orifice;
  advancing the cutting member beyond the distal end of the delivery catheter and through the second orifice, wherein a distal end of the cutting member includes an atraumatic coil tip;
  capturing a distal end portion of the cutting member with a distal end portion of the capture member;
  withdrawing the distal end portion of the capture member in a proximal direction through the first lumen to position a cutting region formed in the cutting member around a portion of one of the anterior or posterior leaflets of the mitral valve adjacent to the edge-to-edge repair device; and
  applying electrical energy to the cutting member to cause the cutting region to cut through a portion of the tissue of one of the anterior and posterior leaflets adjacent to the edge-to-edge repair device to detach the edge-to-edge repair device from the at least one of the anterior or posterior leaflets.

13. A device for at least partially detaching an edge-to-edge repair device that holds together anterior and posterior leaflets of a mitral valve of a human heart, the device comprising:
  an elongate member having a proximal end, a proximal end portion, a distal end portion and a distal end, the elongate member comprising:
    a guiding catheter with a distal end portion that can be selectively bent to reorient the distal end portion of the elongate member;
    a delivery catheter coaxially located within the guiding catheter, the delivery catheter comprising:
      a delivery catheter shell having a first lumen and a second lumen, each extending from a proximal end to a distal end of the delivery catheter shell;
      a first tubular member having a distal end portion and positioned within the first lumen and being moveable in an axial direction relative to the delivery catheter shell; and
      a second tubular member having a distal end portion and positioned within the second lumen and being moveable in an axial direction relative to the delivery catheter shell;
    a capture member extending through the first tubular member and being movable in an axial direction relative to the first tubular member, the capture member having a self-expanding, shape-memory loop formed at a distal end thereof; and
    a first cutting member extending through the second tubular member and being movable in an axial direction relative to the second tubular member, the first cutting member comprising an electrically conductive core extending its entire length, an electrically insulative coating covering a major portion of the conductive core, one or more uncoated, electrically conductive cutting regions, and, a distal end that includes an atraumatic coil tip.

14. The device of claim 13, wherein one or both of the first and second tubular members include a preferential, shape-memory or heat shape bend in the distal end portion thereof.

15. The device of claim 13, wherein the first cutting member comprises a first cutting region and a second cutting region, wherein the first cutting region is disposed at a proximal end of the cutting member and the second cutting region is disposed between the proximal end and a distal end of the cutting member.

16. The device of claim 15, wherein the first cutting region is disposed at and forms a distal end of the first cutting member, proximal of the atraumatic coil tip.

17. The device of claim 13, wherein the first cutting member further comprises one or more radiopaque markers defining peripheral bounds of the cutting regions.

18. The device of claim 13, wherein the capture member comprises a self-expanding, shape-memory loop portion for capturing the first cutting member.

19. The device of claim 18, wherein the loop portion comprises a narrowed portion configured to facilitate preferential collapsing of the capture member upon drawing the capture member into the second tubular member.

20. The device of claim 18, wherein the capture member further comprises one or more radiopaque markers defining peripheral bounds of the loop portion.

* * * * *